United States Patent
Sharma et al.

(10) Patent No.: US 7,177,680 B2
(45) Date of Patent: *Feb. 13, 2007

(54) FIELD STIMULATION ABOUT A DISCONTINUITY OF THE MYOCARDIUM TO CAPTURE THE HEART AT REDUCED PACING THRESHOLDS

(75) Inventors: Vinod Sharma, Blaine, MN (US); Xiaohong Zhou, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 600 days.

This patent is subject to a terminal disclaimer.

(21) Appl. No.: 10/403,636

(22) Filed: Mar. 31, 2003

(65) Prior Publication Data

US 2003/0191502 A1    Oct. 9, 2003

Related U.S. Application Data

(63) Continuation-in-part of application No. 10/308,302, filed on Dec. 3, 2002.

(60) Provisional application No. 60/337,273, filed on Dec. 3, 2001.

(51) Int. Cl.
*A61N 1/05* (2006.01)
*A61N 1/36* (2006.01)

(52) U.S. Cl. ............... 607/9; 607/122; 607/127; 607/131; 606/32; 606/39; 606/48

(58) Field of Classification Search ............ 606/32, 606/39, 45, 48; 607/9, 119, 122, 125–129, 607/131, 132

See application file for complete search history.

(56) References Cited

U.S. PATENT DOCUMENTS

| | | | | |
|---|---|---|---|---|
| 4,357,946 A | * | 11/1982 | Dutcher et al. | 607/131 |
| 4,548,203 A | * | 10/1985 | Tacker et al. | 607/27 |
| 5,154,183 A | * | 10/1992 | Kreyenhagen et al. | 607/131 |
| 5,522,874 A | * | 6/1996 | Gates | 607/127 |
| 5,545,201 A | * | 8/1996 | Helland et al. | 607/127 |
| 5,964,754 A | * | 10/1999 | Osypka | 606/37 |

OTHER PUBLICATIONS

Fast, Vladimir G., et al., Activation of Cardiac Tissue by Extracellular Electrical Shocks: Formation of 'Secondary Sources' at Intercellular Clefts in Monolayers of Cultured Myocytes, Circulation Research, vol. 82(3), Feb. 23, 1998, pp. 375-385.*

(Continued)

*Primary Examiner*—Robert E. Pezzuto
*Assistant Examiner*—Eric D. Bertram
(74) *Attorney, Agent, or Firm*—Michael C. Soldner; Girma Wolde-Michael

(57) ABSTRACT

Improved pacing thresholds for capturing the heart are achieved by forming a discontinuity in the cardiac tissue of the heart chamber, disposing a pacing electrode at a distance less than a space constant of the cardiac tissue from the discontinuity in the cardiac tissue, and applying a stimulus of a first polarity at an energy insufficient to cause the directly stimulated tissue adjacent to the pacing electrode to propagate a depolarization wave through the cardiac tissue mass of the heart chamber but sufficient to induce a transmembrane potential change at the tissue adjacent to the discontinuity that results in a propagated wave front. Thus, pacing energy is advantageously reduced.

38 Claims, 14 Drawing Sheets

OTHER PUBLICATIONS

Newton, Jonathan C., et al., "Review of Mechanisms by Which Electrical Stimulation Alters the Transmembrane Potential", *Cardiovascular Electrophysiology*, 1999, Feb. 10(2), 234-243.

Sobie, Eric A., et al., "A Generalized Activating Function for Predicting Vitual Electrodes in Cardiac Tissue", *Biophysical Journal*, vol. 73, Sep. 1997, pp. 1410-1423.

Neunlist, Michel, et al., "Spatial Distribution of Cardiac Transmembrane Potentials Around an Extracellular Electrode: Dependence on Fiber Orientation", *Biophysical Journal*, vol. 68, Jun. 1995, pp. 2310-2322.

Dekker, Egbart, "Direct Current Make and Break Thresholds for Pacemaker Electroes on the Canine Ventricle", *Circulation Research*, vol. XXVII, Nov. 1970, pp. 811-823.

Milburn, Tracy, et al., "The Temperature Dependence of Conductance of the Sodium Channel: Implications for Mechanisms of Ion Permeation", *Receptors and Channels*, 1995, vol. 3, pp. 201-211.

Sepulveda, Nestor, et al., "Electric and Magnetic Fields from Two-Dimensional Anisotropic Bisyncytia", *Biophysical Journal*, vol. 51, Apr. 1987, pp. 557-568.

Knisley, Stephen B., et al., "Virtual Electrode Effects in Myocardial Fibers", *Biophysical Journal*, vol. 66, Mar. 1994, pp. 719-728.

Nagatomo, Toshihisa, et al., Temperature Dependence of Early and Late Currents in Human Cardiac Wild-type and Long Q-T ΔKPQ NA+ Channels, *The American Physiological Society*, 1998, pp. H2016-H2024.

Fast, Vladimir G., et al., "Activation of Cardiac Tissue by Extracellular Electrical Shocks: Formation of 'Secondary Sources' at Intercellular Clefts in Monolayers of Cultured Myocytes", *Circulation Research*, vol. 82(3), Feb. 23, 1998, pp. 375-385.

Hidden-Lucent, Franscoise, et al., "Low Chronic Pacing Thresholds of Steroid-Eluting Active-Fixation Ventricular Pacemaker Leads: A Useful Alternative to Passive-Fixation Leads", *PACE*, vol. 23, Nov. 2000 Part II, pp. 1798-1800.

Roth, Bradley, J., et al. "A Bidomain Model for the Extracellular Potential and Magnetic Field of Cardiac Tissue", *IEEE*, 1986, pp. 467-469.

Watanabe, Toshifumi, et al., "Ventricular Action Potentials, Ventricular Extracellular Potentials, and the ECG of Guinea Pig", *Circulation Research*, vol. 57, No. 3, Sep. 1985, pp. 362-373.

* cited by examiner

FIG. 2A
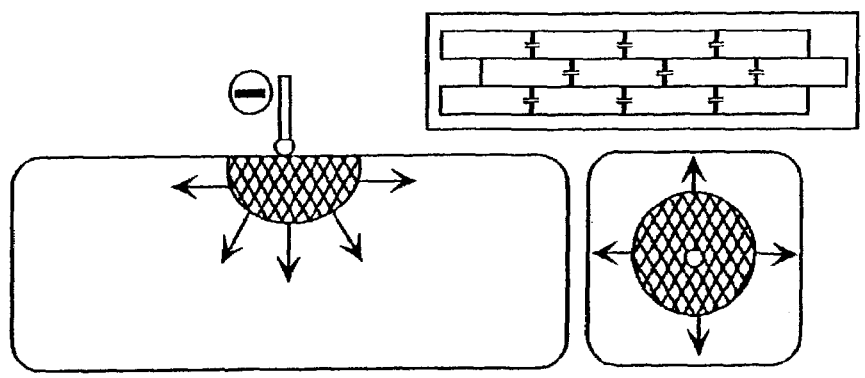
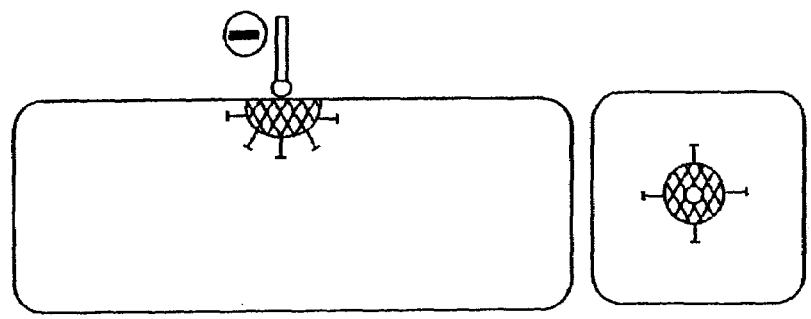
Side View　　　　　Top View
FIG. 2B
Anodal Stimulation　　　　　Cathodal Stimulation
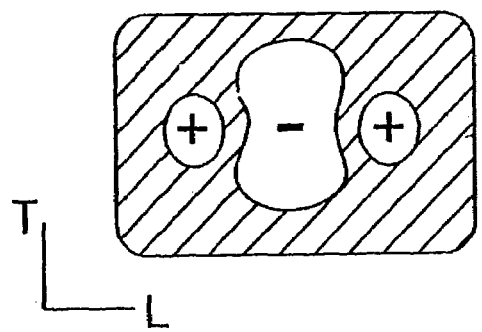
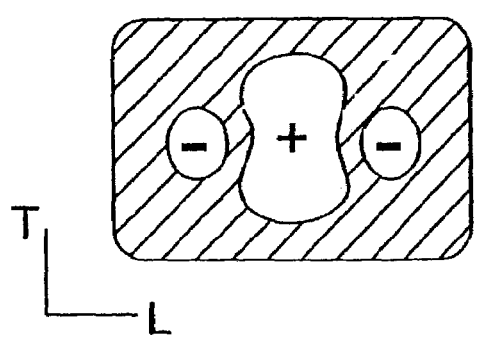
FIG. 3A　　　　　FIG. 3B

FIG. 4A
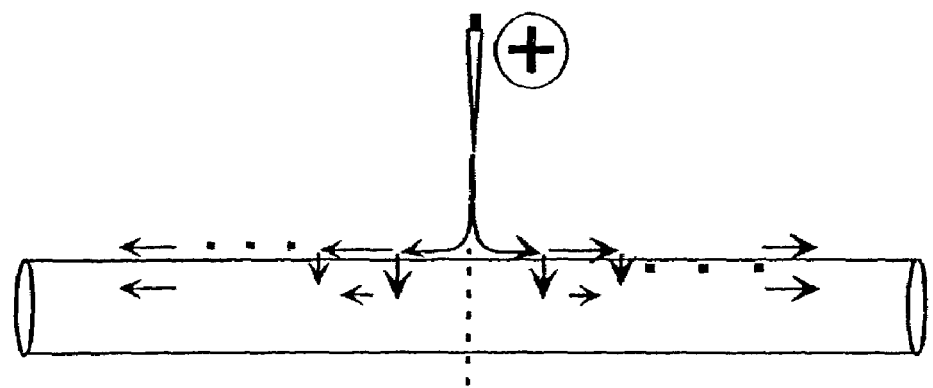
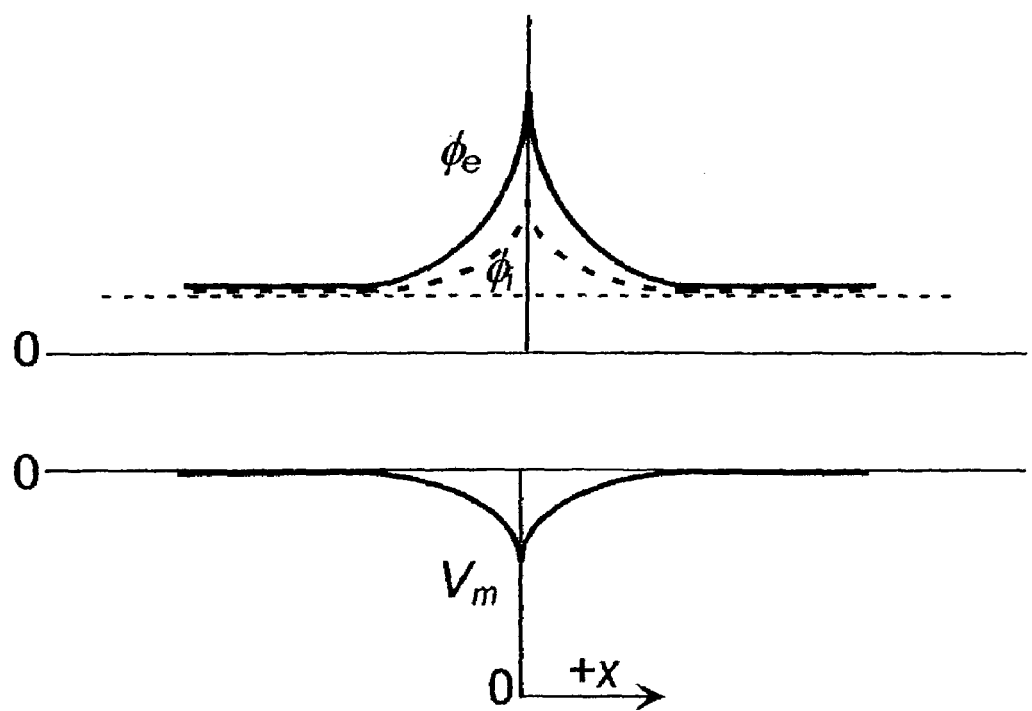
FIG. 4B

FIG. 7
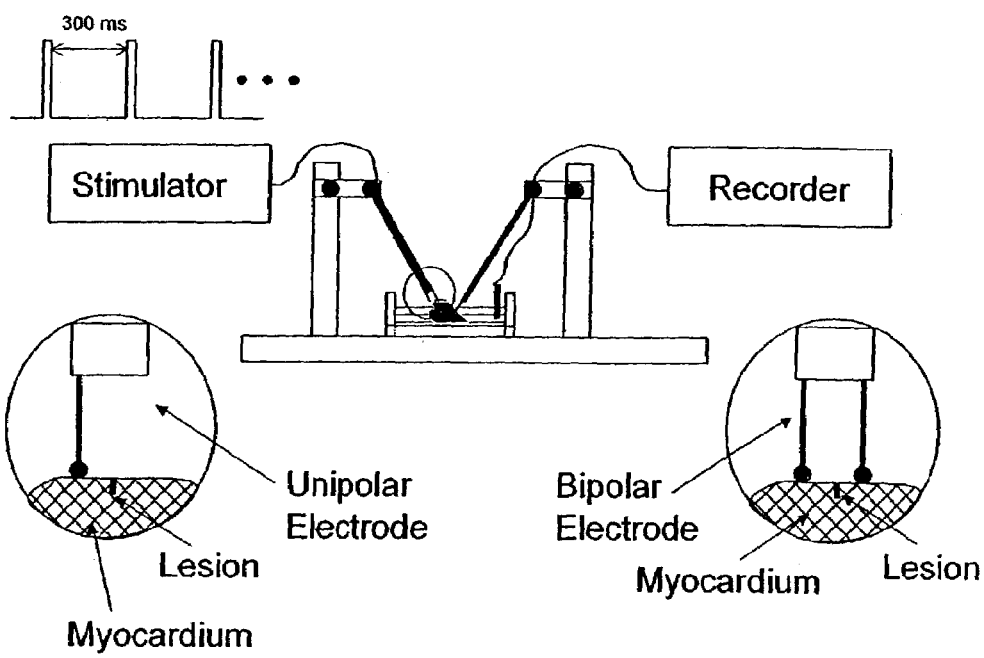
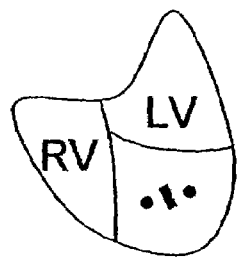
FIG. 8A
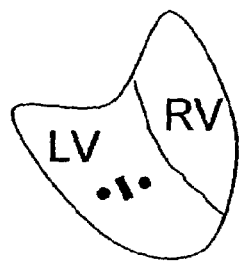
FIG. 8B
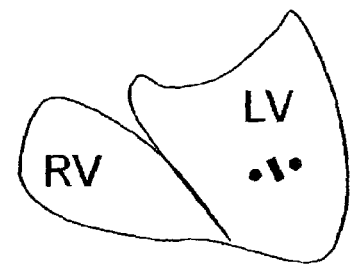
FIG. 8C

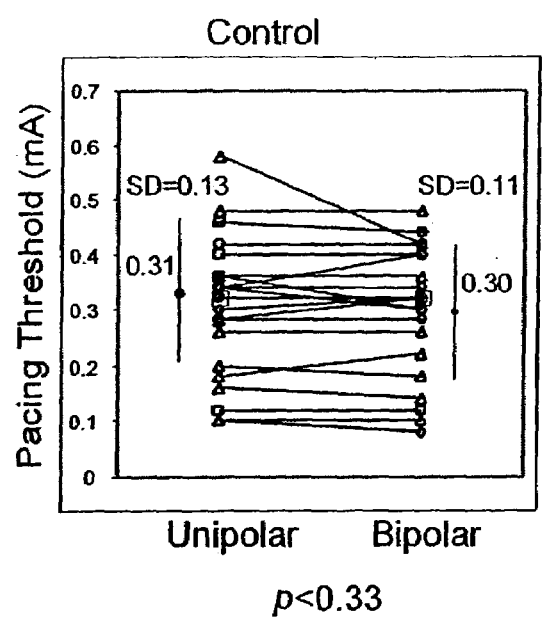 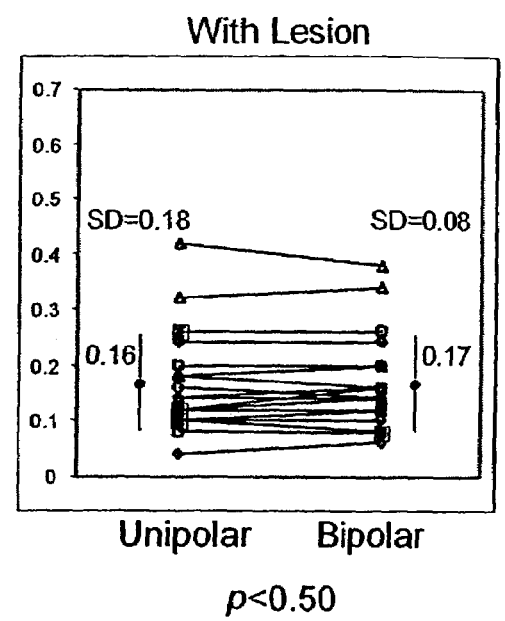
FIG. 14A FIG. 14B

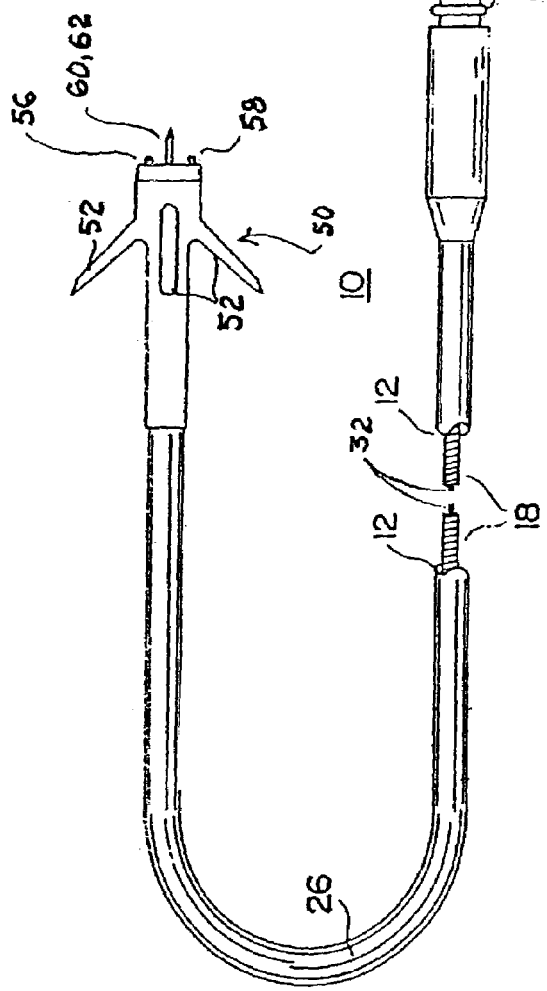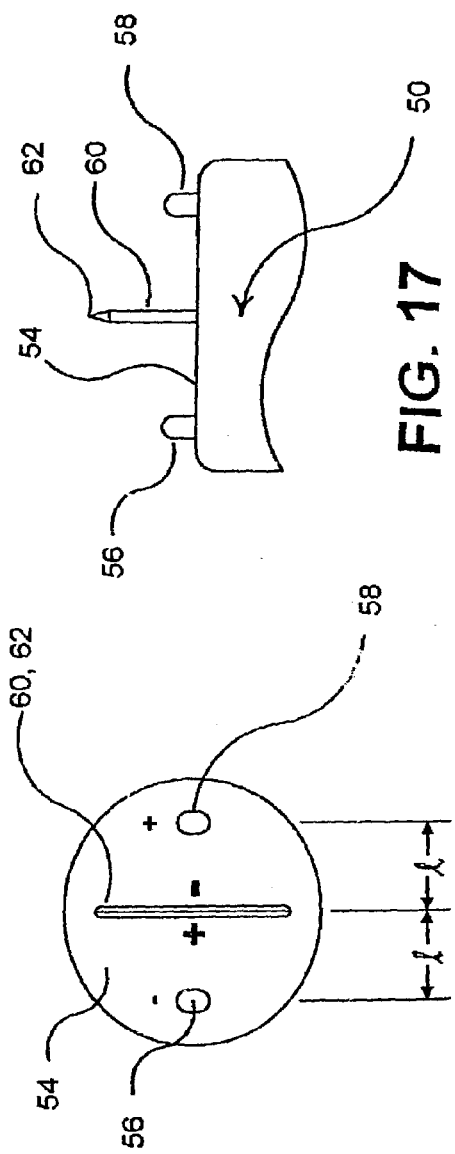

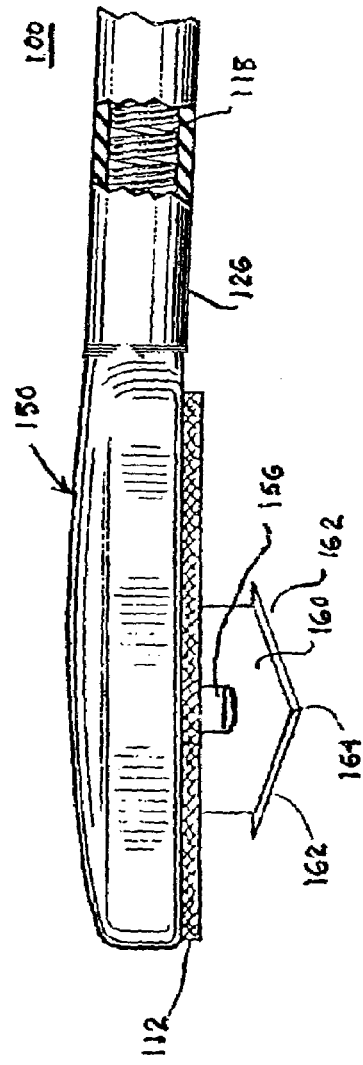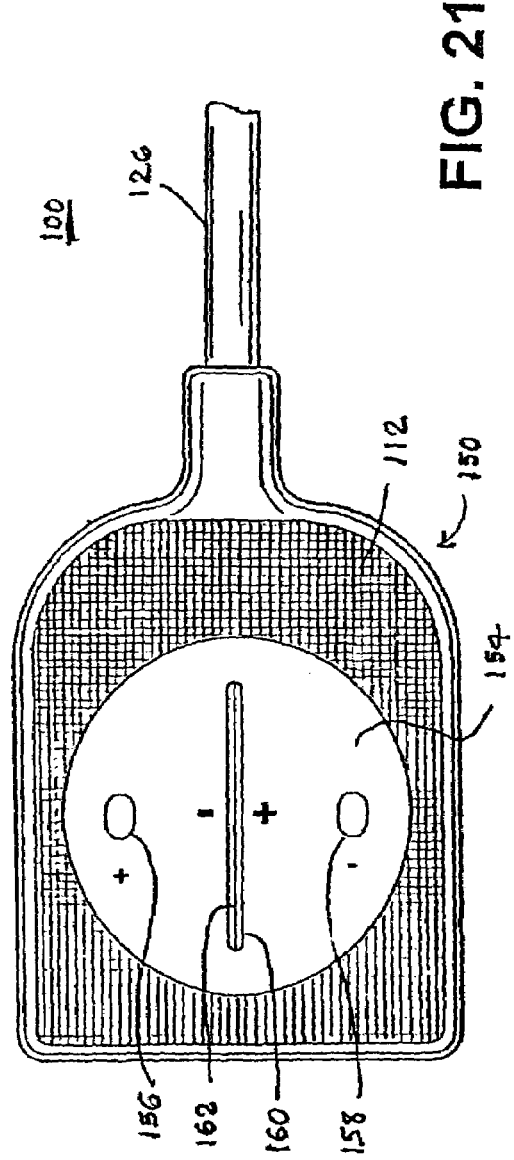

FIELD STIMULATION ABOUT A DISCONTINUITY OF THE MYOCARDIUM TO CAPTURE THE HEART AT REDUCED PACING THRESHOLDS

RELATED APPLICATION

This application is a continuation-in-part of U.S. patent application Ser. No. 10/308,302, filed Dec. 3, 2002, entitled "FIELD STIMULATION ABOUT A DISCONTINUITY OF THE MYOCARDIUM TO CAPTURE THE HEART AT REDUCED PACING THRESHOLDS", which in turn claims priority and other benefits from U.S. Provisional Patent Application Ser. No. 60/337,273 filed Dec. 3, 2001, entitled "PACING VIA VIRTUAL ELECTRODES FORMED AROUND A FIELD STIMULATED MICRO-LESION", both incorporated herein by reference in their entireties.

FIELD OF THE INVENTION

The present invention relates to methods and electrode configurations for pacing the heart, particularly by pacing the heart at reduced pacing energy through inducement of virtual anodes and cathodes along lesions formed in the heart tissue.

BACKGROUND OF THE INVENTION

Many implantable medical devices (IMDs) have been developed over the years for clinical implantation in patient's bodies that deliver electrical stimulation to a body organ, muscle, nerve or brain cells. Each year approximately 750,000 patients develop bradycardia symptoms such as dizziness, extreme fatigue, shortness of breath, or fainting spells. These symptoms are caused by abnormally slow or irregular heart rate, and the most effective method to relieve these symptoms is to implant a pacing system that generates and delivers pacing pulses to a site in or adjacent to a heart chamber. Pacing systems are incorporated into a wide variety of implantable pacemakers and also into implantable cardioverter defibrillators (ICDs). Such pacing systems comprise an implantable pulse generator (IPG) and one or more lead interconnecting the IPG circuitry with pace/sense electrodes implanted against or into the myocardium of the heart.

Each heart cell contains positive and negative charges due to the selective permeation of certain ions, such as potassium and sodium through the cell membrane. When the cell is at rest, the inside of the cell is negatively charged with respect to the outside. The negative charge is dissipated when the cell is disturbed by an electrical signal that causes the permeability of the cell membrane to change and allows the ingress of positive charge ions. The resulting dissipation of the negative charges constitutes the "depolarization" of the cell. Simultaneously, the cell contracts causing (in conjunction with the contraction of adjoining cells) the heart muscle to contract. Thus, the stimulation of the heart muscle affects both the depolarization and the contraction of the once-polarized myocardial cells that make up the muscle.

Following depolarization and contraction of a heart cell, the "repolarization" or recovery of the cell commences so that the cell is ready to respond to the next applied stimulus. During the repolarization time interval, the cell membrane begins to pump out the positive-charged ions that have entered following the application of the stimulus, that is, during the depolarization of the cell. As these positive charges leave, the inside of the cell membrane starts to become negative again, the cell relaxes, and the potential difference builds up again.

The individual myocardial cells are arranged to form muscle fibers and sheets that, in gross, constitute the heart itself. The depolarization of the atrium is characterized by a P-wave viewed on an electrocardiogram (ECG), and depolarization and repolarization signals of the ventricle, are referred to as the QRS complex and the T wave, respectively. The sequence of depolarization, which manifests itself in a contraction of the heart muscle, and repolarization, which manifests itself in the relaxation and filling of the interior chambers of the heart with blood, is accomplished through a system of specialized muscle tissue that functions like a nerve network. Depolarization signals are generated in the SA node of specialized cardiac cells located in the atria at a rate that is appropriate for the body's physiologic demand for cardiac output. The system then conducts these impulses rapidly to all the muscle fibers of the ventricles, ensuring coordinated, synchronized pumping.

When this system fails, or is overridden by abnormal mechanisms, a pacing system may be needed to generate and deliver trains of pacing pulses through pace/sense electrodes to maintain proper heart rate and synchronization of the filling and contraction of the atrial and ventricular chambers of the heart. The pacing circuitry of pacemaker and ICD IPGs is powered by a battery, and each delivered pacing pulse consumes a discrete bolus of the battery energy. Consequently, the IPG longevity is primarily governed by the battery lifetime. Currently, the IPG longevity can range from approximately 3 to 10 years depending on the type of IPG (e.g., pacemaker or ICD). The IPG must be replaced when the battery is depleted, an expensive procedure that also poses significant discomfort and risk to the patient.

The pacing current drawn by each pacing pulse is a major factor that impacts the battery life and device longevity, although its impact is greater for some devices than the others. For example, recently developed bi-ventricular pacing systems incorporated into pacemakers and ICDs present a high current drain since two pacing pulses must be delivered to synchronously pace both ventricles at a pacing rate that typically depends upon the patient's physiologic need for cardiac output as determined by an activity sensor, for example. Thus, the reduction in delivered pacing current would certainly increase the IPG longevity and could allow the battery and corresponding IPG size to be reduced, and therefore positively impact lives of thousands of patients receiving battery powered IMDs.

In the history of implantable cardiac pacemakers, great strides have been made in increasing longevity, reliability, and versatility of IPGs and the associated lead systems. In the early days of implantable cardiac pacemakers, battery depletion was rapid, leading to exhaustion of the IPG batteries within a year from implantation. The high energy consumption was due to a wide variety of factors, including battery self discharge, pace/sense electrode-tissue interface inefficiencies requiring delivery of high energy pacing pulses, and high current consumption by discrete electronic circuit components.

It was recognized from the outset of cardiac pacing that IPG battery current drain is directly proportional to the amount of energy that is necessary when delivered to the heart to cause the heart to depolarize, i.e., to "capture" the heart. Over the last forty years, reliability and longevity have dramatically improved due to improvements in battery technologies, lead and pace/sense electrode technologies, electronic circuitry current consumption and a wide variety of other areas. As improvements in one area led to increased longevity and reliability, attention was focused on the other areas.

In this evolutionary process, early studies were conducted to determine if the optimum stimulation pulse polarity and wave shape could be found that would achieve capture of the heart at the lowest expenditure of pulse energy in order to prolong pacemaker battery life as reported, for example, by Egbert Dekker, M. D., in "Direct Current Make and Break Thresholds for Pacemaker Leads", (*Circulation Research*, vol. XXVII, November 1970, pp. 811–823). In the infancy of cardiac pacemakers, experiments were performed using various forms of electrical stimulation pulses including anodal (positive going) and cathodal (negative going) pacing pulses having pulse energy exceeding the stimulation threshold to trigger depolarization of myocardial cells.

Contemporaneously, attention was focused on other factors, particularly pace/sense electrode technologies, high energy density, low self discharge, battery technology, variable pulse energy output pulse circuits, and capture threshold determination techniques that made dramatic improvements in IPG longevity, reliability and size. The pace/sense electrode technologies have included pace/sense electrode materials including substrates, coatings and surface treatments, pace/sense electrode shapes, pace/sense electrode surface areas, and pace/sense electrode configurations as well as minimizing local tissue injury when the pace/sense electrode fixed in place by a tissue penetrating active fixation mechanisms, delivery of steroids to the stimulation site by incorporation of steroid eluting elements in the lead body adjacent to the fixation mechanism or coatings on the fixation mechanism.

Today's implantable pacemakers and pacing systems incorporated into ICDs are far more versatile and offer a wider variety of therapies for medical conditions that were not imagined in the infancy of cardiac pacing. Currently, electrical stimulation generated by a pacemaker or ICD IPG is in the form of pacing pulses typically having a fixed duration in the order of about 0.5 ms, a voltage of less than 5 volts, and a resulting delivered current dependent upon the collective impedance or load that the pulse is delivered through a cardiac lead conductor and the pace/sense electrode-tissue interface at an active pace/sense electrode. The exponential decaying voltage, cathodal (negative going) pacing pulse shape achieved by a relatively simple, monophasic capacitive discharge output circuit has become accepted as the standard pacing pulse for many years.

Thus, a negative voltage pulse is typically delivered at the active pace/sense electrode, whereby the active pace/sense electrode is characterized as a cathode pace/sense electrode and the return or indifferent pace/sense electrode in the discharge path is characterized as an anode pace/sense electrode. A cathodic electrical field of sufficient strength and current density has to be impressed upon the excitable tissue in the vicinity of the active site to initiate conduction of a depolarization wave through the entire cardiac tissue mass of a heart chamber that causes the heart chamber to contract and expel blood from the heart chamber, i.e., to capture the heart. The minimum pacing pulse energy necessary to produce that effect is referred to as the "stimulation threshold" or "pacing threshold." The greater the efficiency of the cathode in impressing the electric field on the tissue, the smaller is the amplitude and/or duration of the pulse required to exceed the stimulation threshold. With the widespread adoption of multi-programmable parameters including programmable pulse width and amplitude, physicians have become accustomed to determining the patient's pacing threshold and setting the energy level to a minimum value to capture the heart plus an adequate safety margin.

Despite these efforts and realized improvements, a need remains to further reduce pacing thresholds.

SUMMARY OF THE INVENTION

The present invention provides improved pacing thresholds through adoption of technologies that heretofore have not been employed in the provision of pacing via pace/sense electrodes to a heart chamber.

Improved pacing thresholds for capturing the heart are achieved by forming a discontinuity in the cardiac tissue of the heart chamber, disposing a pacing electrode at a distance less than a space constant of the cardiac tissue from the discontinuity in the cardiac tissue, and applying a stimulus of a first polarity at an energy insufficient to cause the directly stimulated tissue adjacent to the pacing electrode to propagate a depolarization wave through the cardiac tissue mass of the heart chamber but sufficient to induce a transmembrane potential change at the tissue adjacent to the discontinuity that results in a propagated wave front. Thus, pacing energy is advantageously reduced employing the methods and apparatus of the present invention.

The present invention is preferably implemented in unipolar and bipolar pacing leads having an electrode head at the lead body distal end wherein the electrode head supports at least one active, cathodal pacing electrode to bear against or be disposed into the myocardium at the space constant distance from the discontinuity. In a bipolar pacing lead, the electrode head supports the active, cathodal pacing electrode and the indifferent, anodal pacing electrode with the discontinuity formed between the pacing electrodes at the space constant distance from each pacing electrode.

The lesion or cleft is preferably created by a non-conductive cutting blade or fixation screw supported by the electrode head to be directed into the myocardium upon fixation of the electrode head against the endocardium or epicardium.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein:

FIGS. 2A and 2B are schematic illustrations of excitation of an isotropic cardiac tissue;

FIGS. 3A and 3B are schematic illustrations of excitation of realistic anisotropic cardiac tissue with unequal anisotropy ratio in the extracellular and intracellular domain;

FIGS. 4A and 4B are graphical depictions of steady state polarization of a cardiac fiber;

FIG. 7 is a schematic illustration of an experimental setup for determining pacing thresholds in cardiac tissue prior to and following forming a lesion in the cardiac tissue;

FIGS. 8A–8C are schematic illustrations depicting stimulation sites of heart chambers of hearts stimulated using the test setup of FIG. 7;

FIGS. 14A and 14B are graphical depictions comparing unipolar and bipolar pacing thresholds prior to and following formation of lesions in guinea pig hearts subjected to threshold testing using the test setup of FIG. 7;

FIG. 15 is a plan view of a first embodiment of a pacing lead incorporating a retractable and extendable cutting blade made from an insulating material for forming a discontinuity in cardiac tissue between anodic and cathodic pacing electrodes disposed on an electrode head distal end;

FIG. 16 is an expanded end view of the electrode head distal end of the lead of FIG. 15;

FIG. 17 is an expanded side view of the electrode head distal end of the lead of FIG. 15;

FIG. 20 is a side view of an electrode head of an epicardial pacing lead that supports a cutting blade to form a discontinuity in cardiac tissue between the anodic and cathodic pacing electrodes;

FIG. 21 is a bottom view of the electrode head of FIG. 20;

Figure 1A:
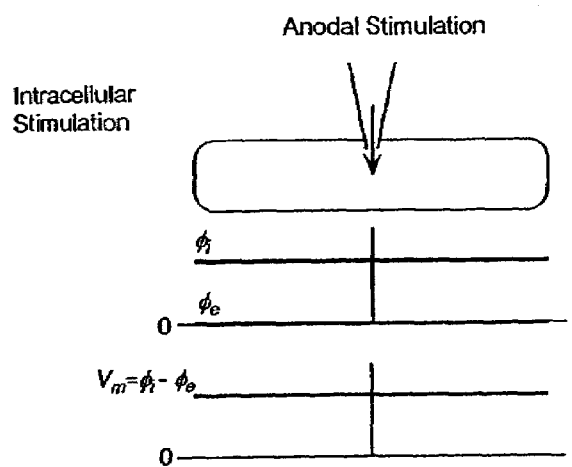
FIGS. 1A and 1B are graphical depictions of anodal and cathodal, intracellular stimulation.

The drawing figures are not necessarily to scale.

DETAILED DESCRIPTION OF THE INVENTION

In the following detailed description, references are made to exemplary embodiments for carrying out the invention in reducing pacing thresholds of chronically implanted endocardial or epicardial pacing leads. It is understood that other embodiments may be utilized without departing from the scope of the invention. The invention and its preferred embodiment may be implemented in unipolar, bipolar or multi-polar, cardiac pacing leads having one or more pace/sense electrode(s) at or adjacent the lead body distal end. The lead is adapted to be coupled to the connector assembly of an implantable pulse generator (IPG) for pacing the heart though the pace/sense electrode(s).

In seeking to lower pacing thresholds, it is first advisable to explore how applied pacing pulses cause the heart to depolarize the heart. Below, we first discuss the electrical excitation of a single cell, the basic unit of cardiac tissue, and then discuss the response to applied stimulation at the tissue level. For simplicity, we start with a discussion of pacing by treating the myocardium as an isotropic medium. This is followed by discussion of pacing in the context of more realistic (but more complex) anisotropic bidomain model. See, Roth et al., "A bidomain model for the extracellular potential and magnetic field of cardiac tissue". *IEEE Trans Biomed Eng.* 1986;33:467-9. Then, we discuss the concept of virtual sources and virtual electrodes that we have explored experimentally to develop new pacing methods and electrodes of the present invention to lower the pacing threshold by an appreciable amount, e.g., 50% or more, of the currently attained values.

Excitation of a Single Cell

A typical mammalian cardiac cell is cylindrical in shape, approximately 120 μm in length and 20 μm in diameter. A single cardiac cell can be excited either by intracellular stimulation illustrated in FIGS. 1A and 1B or by extracellular stimulation illustrated in FIGS. 1C and 1D. In FIGS. 1A–1D, the horizontal axis is space or distance, and the vertical axis is either extracellular potential ($\Phi_e$) or intracellular potential ($\Phi_i$) or transmembrane potential ($V_m$). Note that an electrode of a given polarity can depolarize or hyperpolarize the cell depending on its extracellular or intracellular location.

Figure 1B:
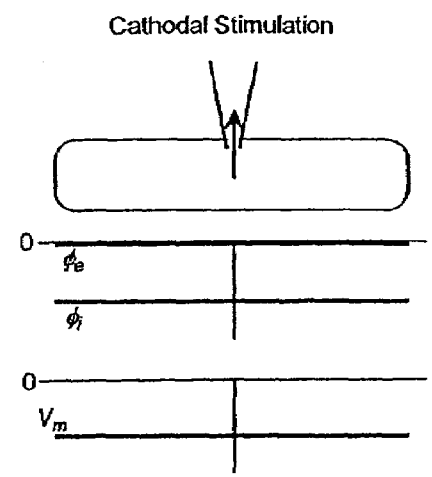

In FIGS. 1A and 1B, a micro-electrode (e.g. a micropipette) is used to impale the cell membrane so that the micro-electrode penetrates into and is continuous with the intracellular space. The intracellular micro-electrode can then be used to inject or withdraw current from the cell. The intracellular micro-electrode can be referred to as an "anodal electrode" when positive (anodal) current is injected into the cardiac cell and as a "cathodal electrode" when negative (cathodal) current is injected into the cardiac cell.

For example, in FIG. 1A, anodal current is injected into the cell through the intracellular micro-electrode that raises the intracellular potential $\Phi_i$ relative to the extracellular potential $\Phi_e$. The increase in intracellular potential is uniform along the cell length because the cell is small in size and has high intracellular conductivity. As a result, the transmembrane potential ($V_m = \Phi_i - \Phi_e$) is raised, and the cell is depolarized. The conductance of sodium channels (small proteins spanning the cell membranes) undergoes a very rapid increase when the transmembrane potential $V_m$ attains a threshold value (~−60 mV from resting value of ~−90 mV). Sodium ions then flood the intracellular space and further raise the transmembrane potential $V_m$ resulting in a cascade of time-dependent and voltage-dependent changes in the conductance of other cell membrane channels (e.g., $Ca^{2+}$ and $K^+$ channels) causing the cell to fire an action potential.

However, the cell is hyperpolarized and not depolarized if cathodal current is injected into the cell through the intracellular micro-electrode as shown in FIG. 1B. The intracellular potential $\Phi_i$ is lowered relative to the extracellular potential $\Phi_e$. Again, the decrease in intracellular potential is uniform along the cell length because the cell is small in size and has high intracellular conductivity.

Figure 1C:
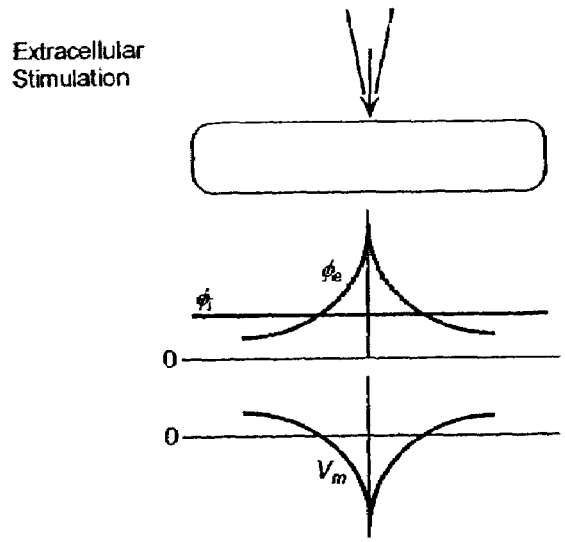
FIGS. 1C and 1D are graphical depictions of anodal and cathodal, extracellular stimulation.
Figure 1D:
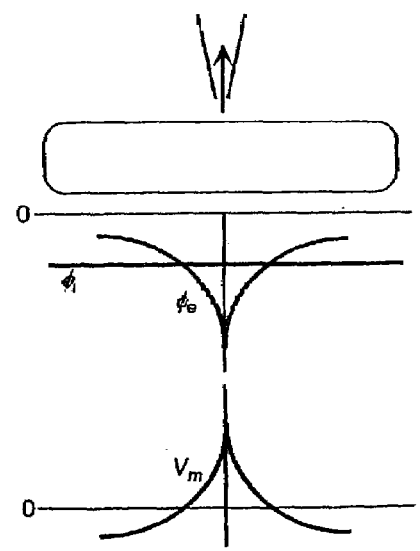

As shown in FIGS. 1C and 1D, a single cardiac cell can be stimulated with an extracellular electrode disposed outside the cell membrane. The application of positive (anodal) stimulation through the extracellular electrode results in a positive extracellular potential $\Phi_e$ that falls monotonically with distance from the electrode. The intracellular potential $\Phi_i$ is raised to a uniform value that is a weighted average of extracellular potential $\Phi_e$ around the cell. Thus, the trans-membrane potential $V_m$ has the profile shown in FIG. 1C. Note that the center of the cell now is hyperpolarized. Thus, the excitation would occur only if the depolarization at the ends of the cell exceeds the threshold value, and would require a large extracellular current. If, however, the polarity of the electrode is reversed to apply negative (cathodal) stimulation, the transmembrane potential $V_m$ profile is reversed as shown in FIG. 1D. In this case, the cell center is depolarized resulting in easier cell excitation.

Thus, a cardiac cell can be excited by anodal or cathodal stimulation applied through respective anodal or a cathodal stimulating electrodes, depending on stimulating electrode location (extracellular versus intracellular).

Modeling Myocardium as an Isotropic Medium

To date, chronically implanted pace/sense electrodes (i.e., electrodes employed to deliver pacing pulses and to sense intrinsic heart signals) coupled with pacemaker or ICD IPGs are not designed to and cannot penetrate a viable cell membrane to apply intracellular stimulation to a single cardiac cell. Any penetration of cardiac cells that may occur during implantation or fixation of a pace/sense electrode into the myocardium irreparably damages the cell(s) and results in scar tissue contacting the electrode or fixation mechanism. Therefore, when pacemaker or ICD IPGs generate and deliver narrow pulse width (~0.5 ms), negative going or cathodal pulses to a pacing site of the heart in order to pace a heart chamber, the pacing current is injected in the extracellular space. The cathodal pacing pulse is generated by discharge of a capacitor, typically charged to a voltage of 5 volts or less between discharges, through a discharge circuit or load. The discharge load comprises the lead conductor(s), the cathodal, active pace/sense electrode at the pacing site, an anodal return or indifferent pace/sense electrode, the cardiac and other body tissues and fluids between the active and indifferent pace/sense electrodes, and the electrode-tissue interfaces at the electrode surfaces. The active pace/sense electrode is located typically at the distal end of a cardiac lead, and the indifferent pace/sense electrode is either located on the same lead or located more remotely, typically on the conductive housing of the IPG. The active pace/sense electrode either is fixed to bear against the endocardial or epicardial heart surface (referred to as passive fixation) or penetrates through the endocardial or epicardial heart surface into the myocardium (referred to as active fixation).

For a single cardiac cell that is stimulated with an extracellular electrode shown in FIG. 1D, the pacing pulse must raise the transmembrane potential, Vm, of a critical length of the cell above a threshold value to cause a regenerative action potential. However, in practice, for a 3-dimensional cardiac tissue the cathodal stimulation energy applied to the extracellular domain through the typical active pace/sense electrode must depolarize a critical volume of the tissue as illustrated in FIGS. 2A and 2B so that the depolarized volume of cells acts as a foci of depolarization of the entire heart chamber. A pacing pulse having a pulse energy exceeding the threshold value and causing the heart chamber to depolarize is said to "capture" the heart. The reason that a depolarization wave produced by a pacing pulse of threshold energy is able to invade the entire heart is that the cardiac tissue is an electrical syncytium in which every cardiac cell is connected to the next cardiac cell via intercellular gap junctions (i.e., small pore-like proteins structures that connect two adjacent cells) as shown in the inset to FIG. 2A. Thus, a trans-membrane current entering into one cardiac cell can be dissipated into an adjacent cardiac cell by electrotonic interaction (source-sink interaction). If the volume of cardiac tissue that is caused to depolarize by the applied cathodal stimulus is below a threshold volume, the current sink is large relative to the source; therefore, the applied excitation fails to result in a conducted depolarization through the cardiac muscle as shown in FIG. 2B. The current sink from the adjacent tissue is so large that the tissue excitation is suppressed. The source-to-sink mismatch decreases with an increase in the amount of tissue directly depolarized by the applied cathodal stimulus. Thus, the applied pacing pulse energy must provide enough current to excite a critical mass of cardiac tissue to result a conducted depolarization to occur that captures the heart.

The amount of cathodal stimulation energy required to excite the critical mass of cardiac cells illustrated in FIG. 2A that in turn captures the heart is referred to as the stimulation threshold or pacing threshold. In practice, the pacing pulse energy (pulse width or pulse voltage) is periodically adjusted by an auto-threshold algorithm or by programming so that the applied pacing pulse energy exceeds the pacing threshold by a sufficient safety margin to conserve battery energy.

From the above discussion any strategy that can decrease source-sink interaction would decrease the critical mass required for excitation, and consequently will decrease current consumption and prolong battery life. In accordance with the present invention, we manipulate the cardiac tissue precisely to accomplish this goal. But before we examine how such manipulation of cardiac tissue can be accomplished, we must introduce a slightly more complex but more accurate anisotropic model of the cardiac tissue.

Modeling Myocardium as an Anisotropic Medium

The heart as a whole is much more complex than the cells or cell masses depicted in FIGS. 1A–1D and 2A–2B. The cardiac cells that contract and relax in the normal heart cycle and that can be stimulated with a pacing pulse to contract are organized in sheets and fibers that define the muscular atrial and ventricular heart chamber walls, the atrial and ventricular septum, and that merge with tissues that do not contract and relax at the base of the heart and that form valves and arterial and venous valves, etc. The sheets and fibers forming the muscular ventricles change orientation as they wrap longitudinally and transversely around and across the atrial and ventricular walls. Thus, the cardiac tissue is anisotropic in both the intracellular and extracellular domains rather than being an isotropic medium with uniform conductivity in all directions. Moreover, the anisotropy ratio (longitudinal to transverse) is unequal in the two domains (4:1 for extracellular domain versus 10:1 for the intracellular domain). Therefore, the anisotropic cardiac tissue responds to an externally applied stimulus in a very interesting fashion.

Schematically illustrated responses of myocardial fibers to anodal and cathodal extracellular stimuli are illustrated in FIGS. 3A and 3B, where L represents the longitudinal direction and T represents the transverse direction of the myocardial fibers. In FIGS. 3A and 3B, polarized regions or fields of the myocardial fibers that are marked with a "+" are depolarized by an applied stimulus, and polarized regions or fields of the myocardial fibers that are marked with a "−" are hyperpolarized by an applied stimulus. A dog-bone shaped region of depolarization marked "−" and extending in the transverse direction T forms directly beneath a stimulation electrode applying cathodal stimulation to the myocardial fibers as shown in FIG. 3A. Two regions of hyperpolarization marked "+" also form at a distance in the longitudinal direction L away from and flanking the dog-bone shaped region of depolarization marked "−" in response to the applied cathodal stimulation as also shown in FIG. 3A. The depolarization and hyperpolarization regions are reversed in polarity in response to an anodal stimulus applied through the same electrode, such that the central hyperpolarized region marked "+" is flanked by two regions of depolarization marked "−" as shown in FIG. 3B.

These complex hyperpolarization and depolarization patterns appear because the tissue anisotropy alters the flow of current in the intracellular and extracellular domains compared to that in an isotropic medium. A way to conceptualize the two polarization fields flanking the dog-bone shaped field is to think of them as arising from "virtual sources" or "virtual electrodes". These virtual sources/electrodes then can be viewed as polarizing the tissue just like stimuli applied to the tissue by real electrodes at the remote polarization fields. The presence of these virtual sources that were initially predicted theoretically (See Sepulveda et al., "Electric and Magnetic Fields From Two-Dimensional Anisotropic Bisyncytia", *Biophys J.* 1987;51:557-68), has been experimentally verified. See, Knisley et al., "Virtual Electrode Effects in Myocardial Fibers", *Biophys J.* 1994;66: 719-28 and Neunlist et al., "Spatial Distribution of Cardiac Transmembrane Potentials Around an Extracellular Electrode: Dependence on Fiber Orientation", *Biophys J* 1995; 68:2310-22.

Such virtual sources can arise not only from the tissue anisotropy but also from several other factors that disrupt the flow of the intracellular or extracellular currents, e.g., fiber bending, gradient in the extracellular electrical field, and changes in intracellular and extracellular conductance. See Sobie et al., "A Generalized Activating Function for Predicting Virtual Electrodes in Cardiac Tissue", *Biophys J.* 1997;73:1410-23.

The effects of a discontinuity in a single layer of cardiac cells grown on a glass substrate has been investigated by Fast et al. in "Activation of Cardiac Tissue by Extracellular Electrical Shocks—Formation of 'Secondary Sources' at Intercellular Clefts in Monolayers of Cultured Myocytes", *Circ. Res.,* 1998;82:375-385. By using fluorescent means to record electrical activity of the cardiac cells, Fast et al. showed that regions of polarization appear around a hole (referred to as intracellular cleft) in the monolayer in response to uniform field stimulus. Since these regions of polarization appear in the absence of a real electrode at the site of the hole, they can be said to be arising from "virtual sources" we introduce above. Herein, we demonstrate how a discontinuity in the intracellular domain, particularly a discontinuity in intracellular conductivity, can alter intracellular current flow and give rise to virtual sources that can be exploited to reduce pacing thresholds.

For simplicity, consider a fiber of cardiac tissue with zero resting potential as shown in FIG. 4A. Moreover, consider that the fiber is stimulated with anodal stimulation, for example, applied through a very small diameter extracellular electrode at stimulating site x=0. This anodal stimulation applied from a real electrode raises the extracellular potential $\Phi_e$ and depresses the intracellular potential $\Phi_i$ at the site x=0 as shown in FIG. 4B. The transmembrane voltage $V_m$ depicted in FIG. 4B is maximal right beneath the electrode and decays exponentially on either side of the electrode ($V_m = Ae^{-|x|/\lambda}$, where A is a constant that depends on intracellular and extracellular conductivities, membrane resistance, and strength of the source).

Qualitatively, this transmembrane potential $V_m$ profile can be explained as follows. As mentioned above, cardiac cells have ion channels embedded in their membranes, and therefore have finite membrane conductance. Thus, as the current injected by the external electrode flows along the fiber length, it flows across the cell membrane and redistributes between the extracellular and intracellular spaces as shown in FIG. 4A. The steady state current in the two domains depends on the intracellular and extracellular conductivities (e.g. when the two are equal the currents in the two domains are equal as well). As the intracellular and extracellular currents reach steady state, transmembrane potential $V_m$ is negative (hyperpolarized) at the center and decays to zero away from the site of the electrode (x=0).

Figure 5A:
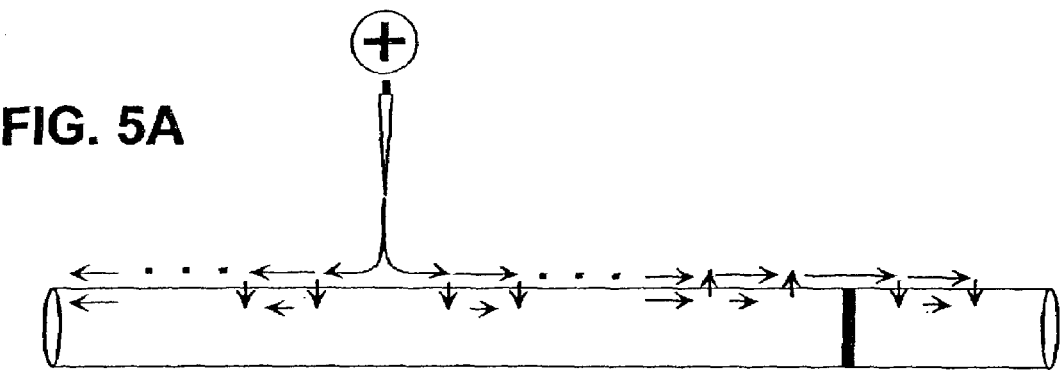
FIGS. 5A–5D are graphical depictions of the formation of virtual sources bracketing an intracellular discontinuity.
Figure 5B:
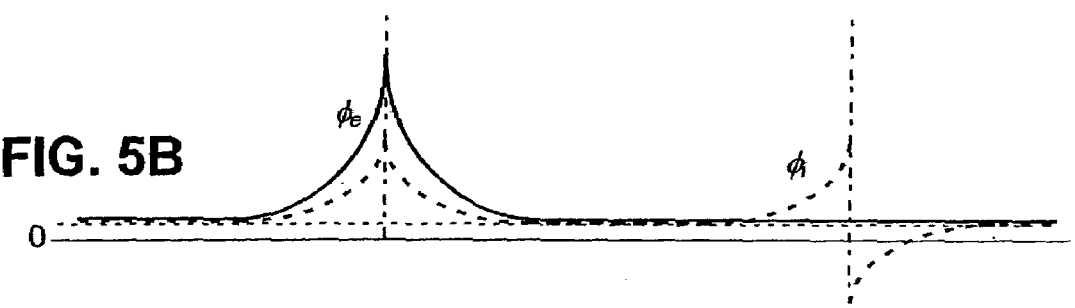

If the intracellular space is discontinuous at a certain "space constant" ($\lambda$) distance (>$\lambda$) from the electrode (at x=0) as shown by the black mark in FIG. 5A, then the flow of intracellular current is impeded as also shown in FIG. 5A. The myocardial space constant $\lambda$ is a function of intracellular resistivity ($r_e$), membrane specific resistance ($r_m$), and extracellular resistivity ($r_i$) determined by $\lambda = \sqrt{r_m/(r_i+r_e)}$. For example, the intracellular current encounters an abrupt barrier caused by an intracellular cleft (no intracellular space) or an intracellular lesion (an induced injury to cardiac cells resulting in scar tissue), and therefore the intercellular current must exit the intracellular space and reenter on the other side of the cleft or lesion. Thus, discontinuity at the cleft or lesion impedes the flow of intracellular current and results in changes in the transmembrane potential $V_m$ far from the electrode (x>$\lambda$) as shown in FIG. 5B.

Figure 5C:
Figure 5D:
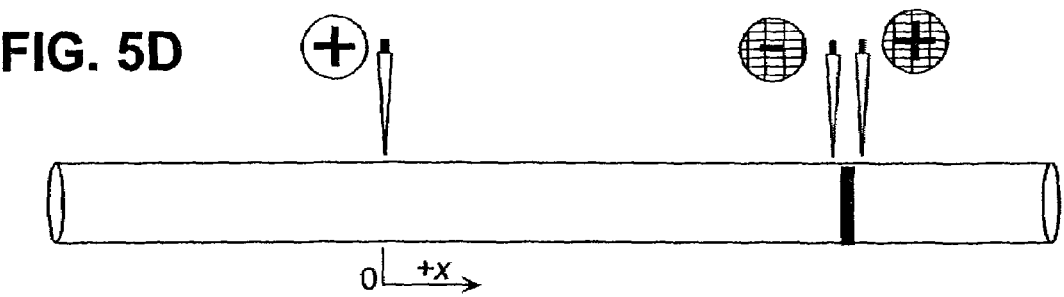

As shown in FIG. 5C, opposite polarity regions of polarization are created on either side of the intracellular discontinuity or cleft or lesion at (x>$\lambda$) that would not be present in the absence of the intracellular discontinuity or cleft or lesion. The pattern of transmembrane potential $V_m$ at (x>$\lambda$) shown in FIG. 5D away from the anodal stimulus applying electrode (at x=0) can be conceptually thought of as arising from a pair of virtual sources that we characterize as "virtual electrodes" at the site of the intracellular discontinuity or cleft or lesion. The cathodic current exiting from the intracellular space on one side of the cleft or lesion closest to x=0 and the accompanied depolarization can be thought to be arising from a virtual cathodal electrode or source indicated at <−> in FIG. 5D. The anodic current and the accompanying hyperpolarization on the other side of the cleft or lesion can be thought to be arising from a virtual anodal electrode or source indicated at <+> in FIG. 4D. The virtual cathodal electrode or source on one side of a discontinuity is referred to herein as a "virtual cathode", and the virtual anodal electrode or source on the other side of the discontinuity is referred to herein as a "virtual anode".

Figure 6A:
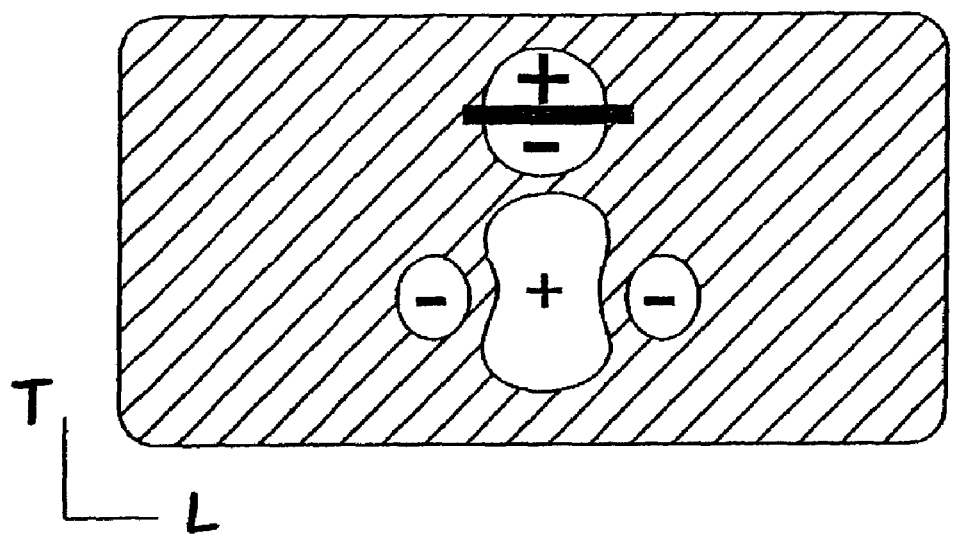
FIGS. 6A and 6B are schematic illustrations of excitation of anisotropic cardiac tissue inducing virtual sources bracketing an intracellular discontinuity.
Figure 6B:
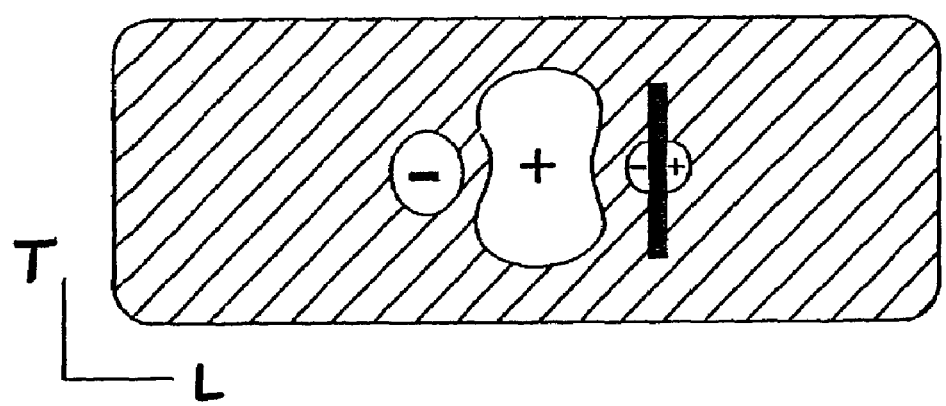

We found the optimal distance x to be ~1.5λ to ~2.5λ. The two-dimensional spatial fields of virtual anodes and virtual cathodes occurring on either side of an intracellular discontinuity, e.g., a cleft or lesion, formed in a cardiac tissue fiber in response to an anodal stimulus, for example, applied to the cardiac tissue fiber at a distance x~1.5–2.5λ from the cleft or lesion are illustrated in FIGS. 6A and 6B. It will be understood that the virtual anodes and virtual cathodes would appear on the opposite sides of the intracellular discontinuity in response to a cathodal stimulus applied to the cardiac tissue fiber at the distance x~1.5–2.5λ from the cleft or lesion. In FIG. 6A, the elongated cleft or lesion is formed in the same direction as the longitudinal direction L of the cardiac tissue fibers. In FIG. 6B, the elongated cleft or lesion is formed transverse to the longitudinal direction L of the cardiac tissue fibers, i.e., in the transverse direction T.

These virtual anodes and virtual cathodes flanking the cleft or lesion are conceptually similar to the hyperpolarization regions marked by "−" flanking the dog-bone shaped depolarization regions marked by "+" below the real cathodal electrode that are also depicted in FIGS. 6A and 6B. As described above, the regions of hyperpolarization flanking the central depolarized region of anisotropic cardiac tissue stimulated with cathodal stimulation depicted in FIG. 3B serve as electrotonic current sinks. The electrotonic current sinks limit the ability of the depolarized region directly stimulated by the real electrode to excite the entire cardiac tissue. As noted above, the current practice is to apply sufficient pulse energy to increase the depolarized region sufficiently to overcome the effects of the electrotonic current sinks.

By contrast, the virtual anode and virtual cathode flanking the cleft or lesion that arise when a stimulus energy is applied at the real electrode site x=0 (FIG. 5) occur entirely due to the presence of the cleft or region and have an entirely different effect upon the depolarization threshold.

First of all, hyperpolarization regions operating as source-sinks as described above with respect to FIGS. 3A and 3B are not associated with the virtual anode and virtual cathode bracketing the cleft or lesion illustrated in FIGS. 6A and 6B. Conceptually, this can thought to be the result of cancellation of such effects from the closely spaced virtual anode on one side of the cleft or lesion and the virtual cathode on the other side of the cleft or lesion.

Moreover, the electrotonic interaction between the virtual anode and the virtual cathode bracketing the lesion will be small, provided the cleft or lesion depicted in FIG. 6A is long enough (i.e., longer than space constant λ). Thus, the electrotonic current sink is minimal at the location of the virtual cathode, and the strength of the cathodic virtual source, and consequently the accompanied depolarization could potentially be stronger than the real source. As a result, the pacing threshold would be reduced, resulting in a reduced pacing pulse energy of a pacing pulses applied at the real electrode sufficient to capture the heart.

Similarly, the lesion may decrease the electrotonic load on the centrally depolarized region and help reduce the pacing threshold if the lesion is made perpendicular to the fibers (i.e. along the transverse direction T) approximately at the location of the hyperpolarization region, as shown in FIG. 6B.

Thus, we postulated that both longitudinal and transverse lesions could potentially lower the pacing threshold when a pacing stimulus is applied through the real electrode at x=0 in FIG. 6A or in FIG. 6B.

It is understood that, although the optimal distance x is described as being ~1.5λ to ~2.5λ, a reduction in pacing threshold can also be achieved by positioning the lesion at a distance less than 1.5λ, albeit not to the extent that results from placing the lesion at a distance of approximately ~1.5λ to ~2.5λ. However, the reduction in pacing threshold achieved when positioning the lesion at a distance less than approximately 1.5λ is a result of a reduction in loading effect on the electrode that occurs when the lesion is formed in cardiac tissue at a distance less than 1.5λ from the stimulation site, since there is a significantly smaller amount of tissue that is required to be excited by the pacing pulse as compared to when no lesion is formed in the cardiac tissue fibers.

Experimental Methods

Experiments were performed on eight isolated guinea pig hearts weighing between 150 and 250 grams. Each guinea pig was anesthetized with an intraperitoneal injection of sodium pentobarbital (0.1 ml/100 g, Abbott Labs, North Chicago, Ill.), and its heart was removed via a radical medial thoracotomy once it failed to respond to the paw pinch reflex test. The heart was then quickly placed in a beaker containing ~50 ml of oxygenated 1.8 mM $Ca^{2+}$ Tyrode (solution) maintained at ~0° C. The beating heart was gently massaged to eject blood from the heart cavity, and quickly mounted on a Langendorff column. FIG. 7 shows the schematic of our experimental setup. During the entire course of the experiment the heart was retrogradely perfused with a 1.8 mM $Ca^{2+}$ Tyrode solution maintained at 36° C.–37° C. The composition of $Ca^{2+}$ free Tyrode (in mM) was: 135 NaCl, 5.4 KCl, 1 $MgCl^2$, 0.33 $NaH_2PO_4$, 5 HEPES, 5 glucose (adjusted to pH 7.4 with NaOH). Glucose (5 mM) and Bovine Serum Albumin (BSA) (1 mg/ml) was added to the solution immediately before experimentation. The heart was completely submerged in the warmed Tyrode solution, and allowed to stabilize for ~15–20 minutes before starting experimentation. The solution temperature was continuously monitored during the stabilization period to ensure that it was within the acceptable range of 36° C.–37° C. The heart's electrical activity was also monitored continuously during the course of experimentation using a pair of monitoring electrodes. One monitoring electrode was placed in contact with the heart wall, and the other monitoring electrode was placed in the bath as shown in FIG. 7. ECG type signals were derived from the monitoring electrodes and used to monitor health of the heart and to determine unipolar and bipolar control pacing thresholds and post-lesion pacing thresholds as explained below.

The unipolar and bipolar pacing electrodes used to stimulate the heart to determine pacing thresholds had surface areas of 1.2 $mm^2$ and were made of porous platinum black, a material similar to one used on pace/sense electrodes of commercially available pacing leads. The pacing electrodes were mounted on a manual micro-manipulator and pressed against the myocardium until a reliable and stable capture response to pacing stimuli was observed.

The three sites on the heart where unipolar and bipolar pacing thresholds were measured comprise an anterior left ventricular site shown in FIG. 8A, a posterior left ventricular site shown in FIG. 8B, and an interventricular septum site shown in FIG. 8C. The right ventricle was cut open along the interventricular connection to access the septum.

During bipolar stimulation, both the active cathodal and the return anodal pacing electrodes were affixed at each of the three sites at an inter-electrode spacing ~5 mm apart. During unipolar stimulation, the lead from the stimulator was removed from the return anodal pacing electrode and connected to another return anodal electrode in the bath. The unipolar and bipolar control pacing thresholds were measured for each site after the initial stabilization period.

A lesion was then formed in the myocardial tissue approximately midway between the two pacing electrodes affixed at each site as shown. The lesion was formed using a scalpel to make a cut ~3–5 mm long and orthogonal to an imaginary line between the two pacing electrodes affixed at each site. The lesion was therefore formed between the two electrodes at a distance l=~2.5 mm from each electrode, resulting in an inter-electrode distance of 2l=~5 mm. The distance l was about ~1.5–2.5λ (the space constant) for the cardiac tissue. The unipolar and bipolar test pacing thresholds were then measured for each site. In some experiments, the stability of the determined test pacing threshold was monitored for 5 minutes (n=7 hearts and n=21 sites) and 10 minutes (n=3 hearts and n=6 sites) durations after the lesion formation.

The unipolar and bipolar, control and test, pacing thresholds were determined by applying a train of constant current pulses (each 0.5 ms in duration with inter-pulse duration of 300 ms) using a Bloom stimulator to each site. The pulse current amplitude was gradually increased in increments of 0.02 mA from a sub-threshold value until capture of the myocardium occurred as revealed by the ECG recordings for every pulse in the pulse train. The current amplitude at which a delivered pulse achieved capture was labeled as the pacing threshold for that site.

For statistical comparison, a two-tailed Student's paired t-test was used to compare the means of various data sets. The statistical correlation between any two parameters was determined by calculating Pearson's correlation coefficient R, and conducting a two-tailed Student's t-test for rejecting the null hypothesis that the slope of the best fit line was zero, and that the parameters were not correlated. Values of $P<0.05$ were considered to be significant.

Experimental Results

Both unipolar and bipolar pacing threshold showed a decrease after the lesion formation (n=26 sites for both electrodes). The mean pacing threshold using unipolar electrodes decreased by ~50% from a control value of 0.31±0.13 mA to 0.16±0.08 mA ($P<0.0001$). The mean pacing threshold using bipolar electrodes also decreased by ~50% from 0.33±0.15 mA to 0.16±0.08 mA ($P<0.0001$). For both unipolar and bipolar electrodes, only 33% of the sites showed an increase in threshold over 5 minutes, and 20% showed an increase over 10 minutes. The worst-case increase was 0.08 mA from the control value.

Figure 9A:
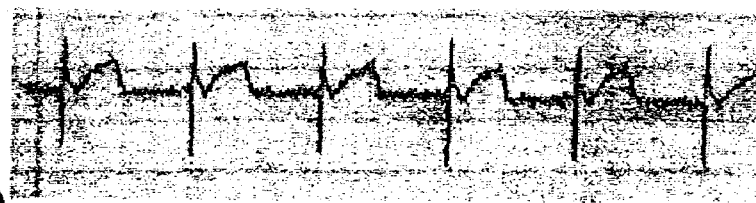
FIGS. 9A–9C are tracings of the cardiac ECG as well as the applied pacing pulses and depolarization responses obtained from a heart stimulated using the test setup of FIG. 7.
Figure 9B:
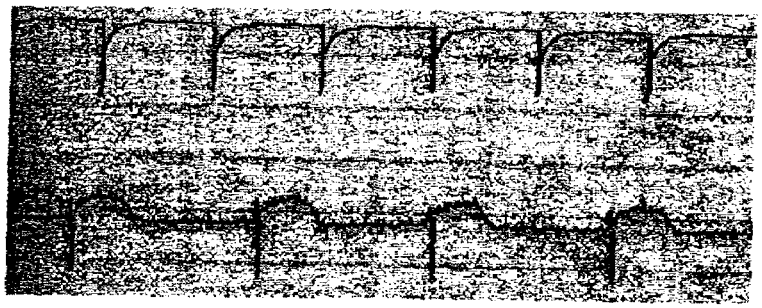
Figure 9C:

As described above, a train of sub-threshold amplitude pacing pulses was applied to the heart to explore the pacing threshold. The recorded ECG reflected sinus rhythm of the heart as shown in FIG. 9A as long as the train of sub-threshold pacing pulses did not capture the myocardium. The pulse amplitude was then gradually raised in increments of 0.02 mA. Myocardial capture occurred for some pulses in the pulse train but not for all as shown in FIG. 9B when the mean pulse amplitude was slightly below the threshold value. However, myocardial capture occurred for every pulse as shown in FIG. 9C when the pulse amplitude was raised by another 0.02 mA, and this pulse amplitude was recorded as the pacing threshold for that site.

Figure 10A:
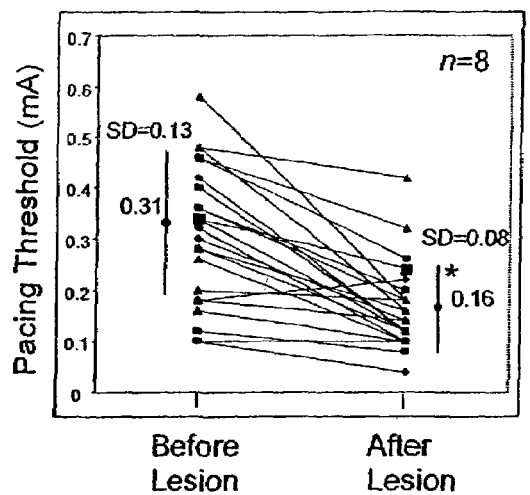
FIGS. 10A and 10B are graphical depictions of pacing threshold data obtained using the test setup of FIG. 7 for unipolar stimulation applied prior to and following formation of linear lesions in guinea pig hearts.
Figure 10B:
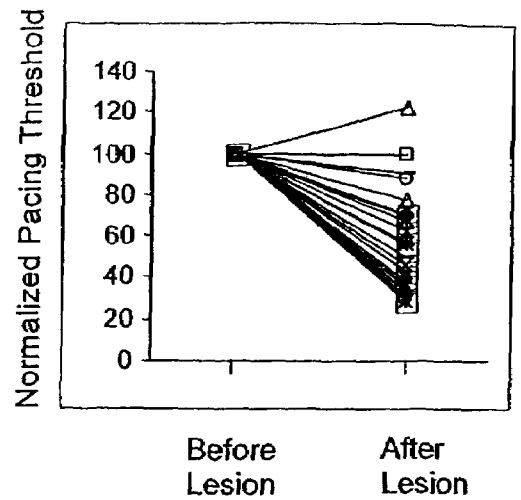

The reduction in pacing threshold after lesion formation is shown in FIG. 10A for unipolar stimulation. The data includes measurement from 26 sites in 8 guinea pigs. The threshold was found to decrease after lesion formation for all sites except one. The mean pacing threshold decreased from 0.31 mA (standard deviation SD=0.13) to 0.16 mA (SD=0.08) after the lesion formation ($P<0.0001$). FIG. 10B shows the same data after normalizing the control threshold to 100%. In some experiments the reduction in pacing threshold was up to 70%.

Figure 11A:
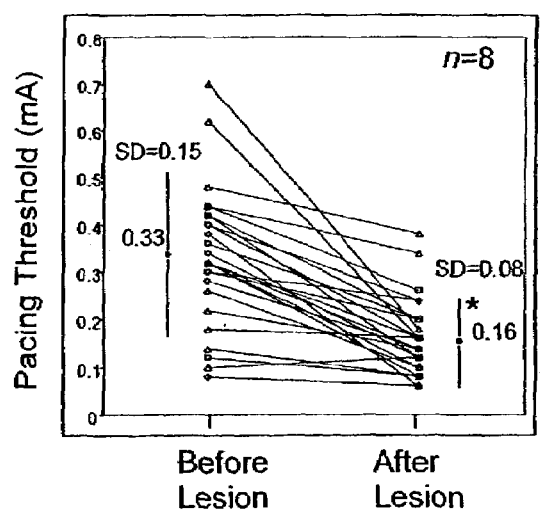
FIGS. 11A and 11B are graphical depictions of pacing threshold data obtained using the test setup of FIG. 7 for bipolar stimulation applied prior to and following formation of linear lesions in guinea pig hearts.
Figure 11B:
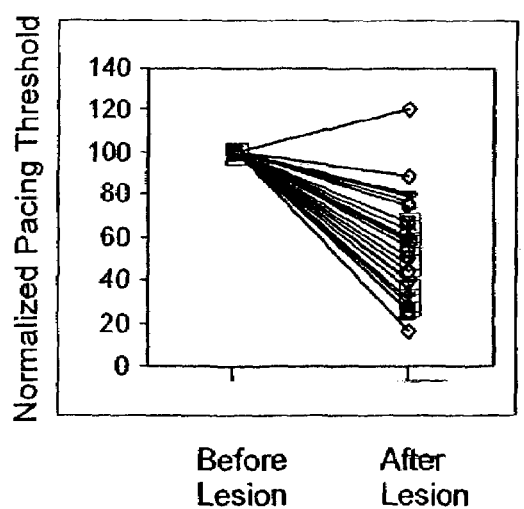

The findings for bipolar stimulation were similar to those for unipolar stimulation. The pacing threshold decreased from 0.33 mA (SD=0.15) to 0.16 mA (SD=0.08) after the lesion formation as shown in FIG. 11A ($P<0.0001$). The normalized data shown in FIG. 11B shows that reduction in pacing threshold for some sites was up to 80%, slightly larger than that observed for unipolar stimulation.

Figure 12A:
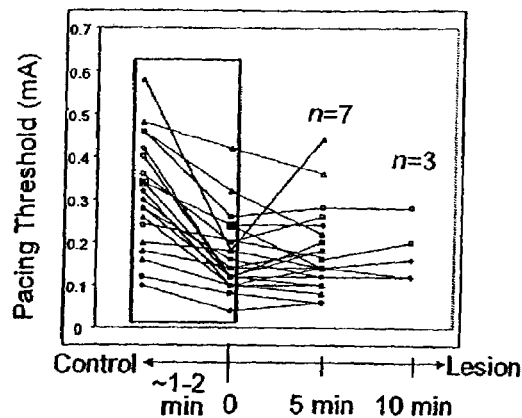
FIGS. 12A and 12B are graphical depictions of time dependent pacing threshold data obtained using the test setup of FIG. 7 for unipolar and bipolar stimulation prior to and following formation of linear lesions in guinea pig hearts.
Figure 12B:
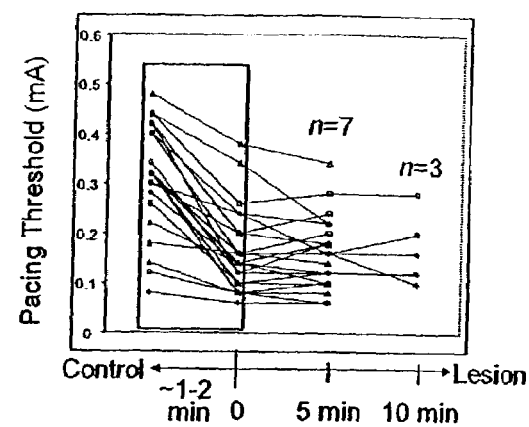

The unipolar and bipolar pacing thresholds measured 5 minutes and 10 minutes after the lesion formation are shown in FIGS. 12A and 12B, respectively. After the 5 minutes wait, 13 sites (~62%) showed a decrease in the pacing threshold, and 7 sites (~33%) showed an increase in the pacing threshold. For unipolar stimulation, the increase in the pacing threshold was restricted to a small range of 0.08 mA for all sites except one exceptional site where the pacing threshold changed by ~0.25 mA. Possible reasons for such a large change in the pacing threshold are discussed below. The pacing threshold increased at only one site after 10 minutes wait, and this increase was less than 0.02 mA. Similar data as set forth in FIG. 12B was obtained in response to bipolar stimulation, except that no unusual increase in pacing threshold was observed. Table 1 depicts percentage of sites with variation in pacing threshold from the control value by various fixed amounts. Note, that the variation in pacing threshold ranged from –0.1 mA to 0.08 mA after 5 minutes wait, and the variation ranged from –0.08 mA to 0.02 mA after 10 minutes wait.

TABLE 1

| | Percentage of total number of sites | | | |
|---|---|---|---|---|
| | Unipolar | | Bipolar | |
| | 5 min* | 10 min | 5 min* | 10 min |
| | Pacing Threshold Change (mA) | | | |
| 0.1 | | | | |
| 0.08 | 4.7% | | | |
| 0.06 | 9.6% | | 4.7% | |
| 0.04 | 9.5% | | 14.3% | |
| 0.02 | 9.5% | 20.0% | 14.3% | 20.0% |
| –0.02 | 38.1% | 40.0% | 47.6% | 40.0% |
| –0.04 | 9.5% | 20.0% | 9.5% | 0.0% |
| –0.06 | 4.8% | 0.0% | 0.0% | 20.0% |
| –0.08 | 0.0% | 20.0% | 4.8% | 20.0% |
| –0.1 | 9.5% | | | |
| | n = 21 | n = 5 | n = 21 | n = 5 |

Figure 13A:
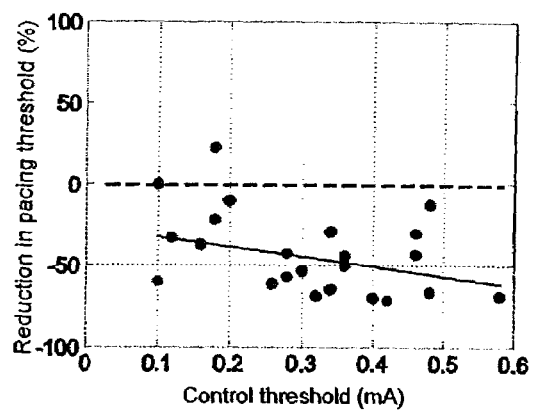
FIGS. 13A and 13B are graphical depictions of the percent reduction in unipolar and bipolar pacing thresholds following formation of lesions in guinea pig hearts subjected to threshold testing using the test setup of FIG. 7.
Figure 13B:
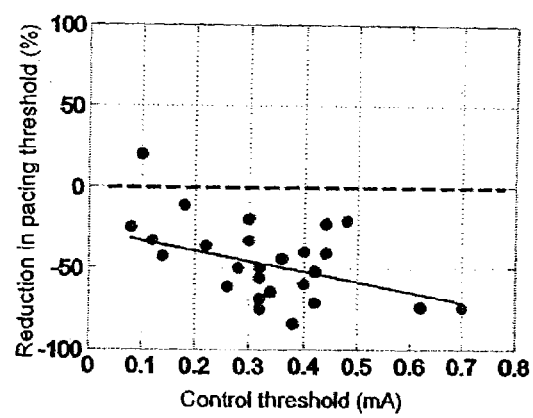

*5 min data exludes one data point with unusually large increase in pacing threshold The reduction in pacing threshold showed a trend of being slightly larger for sites with higher baseline pacing threshold as shown in FIGS. 13A and 13B. The reduction in pacing threshold increased with an increase in the control pacing threshold for both unipolar electrodes as shown in FIG. 3A and bipolar electrodes as shown in FIG. 3B (r=0.36 for unipolar and r=0.44 for bipolar). Although this trend was observed for both unipolar and bipolar stimulation, the slope was greater for bipolar stimulation (–63.4%/mA for unipolar stimulation versus –59.7%/mA for bipolar stimulation).

The pacing thresholds for the unipolar and bipolar stimulation before (control) and after the lesion formation were compared. The control pacing threshold for the two electrodes were approximately equal (0.31±0.13 mA for unipolar versus 0.30±0.17 mA for bipolar; P<0.33) as shown in FIG. 14A. After the lesion formation the pacing threshold for the two electrodes reduced but again remained approximately equal as shown in FIG. 14B (0.16±0.18 mA for unipolar versus 0.17±0.08 mA for bipolar; P<0.17).

These studies of guinea pig hearts support our premise that field-induced virtual anodes and cathode bracketing a linear lesion can reduce the pacing threshold significantly. For unipolar electrodes, the mean pacing threshold was found to decrease from 0.31 mA to 0.16 mA (FIG. 11A), and for bipolar electrodes, the mean pacing threshold was found to be reduced from 0.33 mA to 0.16 mA (FIG. 12A). For some sites, the reduction in pacing threshold was found to be up to 70% for unipolar electrodes (FIG. 11B) and up to 80% for bipolar electrodes (FIG. 12B). The pacing thresholds were found to be quite stable for the majority of the measurement sites for up to 5 to 10 minutes (FIGS. 12A and 12B and Table 1). The reduction in pacing threshold was slightly larger for higher values of baseline pacing threshold for both unipolar and bipolar electrodes (FIGS. 13A and 13B). And finally, for the electrode spacing used in this study, the threshold reduction for unipolar and bipolar electrodes were found to be quite similar (FIGS. 14A and 14B). Thus, we found that field-induced virtual sources around a linear lesion reduce the pacing threshold by ~50% on an average. However, for some sites, a reduction of up to 75–80% was observed suggesting that potentially larger reductions in pacing threshold are possible.

Although we observed a consistent decrease in pacing threshold for most of the sites, this reduction showed significant variation (FIGS. 10 and 11) that may be due to less than ideal control of inter-electrode distance, lesion size and angular orientation to the lesion with respect to tissue fibers and other factors. Although attempts were made to control the temperature within 36–37° C. range, it is possible that in some experiments the temperature exceeded this range for a brief period. Any such fluctuations in solution temperature will cause changes in tissue excitability, and alter the action potential duration. For example, an increase in temperature will make the tissue hyperexcitable because of faster activation (See Nagatomo et al., "Temperature Dependence of Early and Late Currents in Human cardiac Wild-type and Long Q-T DeltaKPQ Na+ Channels", *Am J Physiol.* 1998; 275:H2016-24) and increase conductance of sodium channels (See Milburn et al., "The Temperature Dependence of Conductance of the Sodium Channel: Implications for Mechanisms of Ion Permeation", *Receptors Channels* 1995; 3:201-211) which can decrease the pacing threshold. In contrast, a slight decrease in temperature would cause a prolongation of the action potential.

Considering that the train of pulses used to stimulate the heart had an inter-pulse duration of 300 ms, and guinea pig action potentials are typically 250 ms in duration, this would imply that some of the pulses could have occurred during a relative or absolute refractory period of the action potential. See Watanabe et al., "Ventricular Action Potentials, Ventricular Extracellular Potentials, and the ECG of Guinea Pig", *Circ. Res.* 1985;57:362-373.

Thus, higher amplitude pulses would be required to capture myocardium with every pulse and pacing threshold would be higher. Any other temporal changes in the tissue condition (e.g. its metabolic state) that result in prolongation of action potential would result in an increase in pacing threshold by a similar mechanism.

As is clear from FIGS. 10A–10B and 11A–11B, the control pacing threshold for unipolar and bipolar electrodes varied from 0.1 mA to 0.7 mA. Typically, pacing threshold for normal myocardium should be in the range of 0.3–0.6 mA as derived from voltage and impedance values reported by Hidden-Lucet et al., "Low Chronic Pacing Thresholds of Steroid-Eluting Active-Fixation Ventricular Pacemaker Leads: A Useful Alternative to Passive-Fixation Leads", *Pacing Clin Electrophysiol.* 2000; 23:1798-800. Abnormally low pacing threshold for some hearts might have occurred because the hearts experienced transient global ischemia during the extraction procedure. During ischemia the intercellular gap junctions are partially closed resulting in an increase in intracellular resistivity ($r_e$). Consequently the electrotonic loading effect on the tissue directly depolarized by the electrode is reduced. This would result in a reduction in the critical mass, and therefore in pacing threshold.

The percent decrease in the pacing threshold in hearts with low pacing threshold was found to be smaller compared to the hearts with higher control values as shown in FIGS. 13A–13B. A plausible explanation for this can obtained if we consider that reduction in baseline threshold might be correlated with severity of ischemia experienced by a heart during the extraction procedure. An increase in intracellular resistivity ($r_e$) during ischemia implies that the myocardial space constant [$\lambda=\sqrt{r_m/(r_i+r_e)}$; where $r_m$ is the membrane specific resistance and $r_i$ is the extracellular resistivity] is decreased. Physically, this can be understood in terms of a greater resistance to the flow of intracellular current, which now must exit to the extracellular space over a much shorter distance from the stimulating electrode. As a result, intracellular and extracellular currents equilibrate over a shorter distance, and the space constant is reduced. In our experiments, the lesion was formed in between the two electrodes at a distance l=~2.5 mm from each electrode, resulting in an inter-electrode distance 2l; which was ~5 mm. A decrease in space constant implies that the ratio of lesion-to-electrode distance to the space constant, i.e., $l/\lambda$) increased during ischemia. As a result, the steady state intracellular current had a greater opportunity to spread into surrounding myocardium before reaching the lesion. This would reduce the intracellular current density at the lesion. Since virtual sources arise as a result of perturbation or impediments in the flow of intracellular current, a smaller current density implies an attenuated strength of virtual sources.

We found reduction in pacing threshold for unipolar and bipolar electrodes to be quite similar. This may be the result of the fact that distance between the two electrodes (5 mm) was several times larger than the space constant (~1 mm) of the normal myocardium. Thus, any electrotonic interaction between the two electrodes is expected to be minimal, i.e., current flow pattern from one electrode is unlikely to be influenced by the other electrode. The inter-electrode distance should be of the order of space constant $\lambda$ for a significant electrotonic interaction to occur. However, if the two electrodes were to be a space constant $\lambda$ apart, then the distance between the lesion to any one electrode will be only half a space constant 0.5$\lambda$. This would be insufficient distance for intracellular current density to reach a steady state maximal value. Thus, to maximize the strength of the virtual sources, the two electrodes should at least be two space constants away (2$\lambda$). However, this guarantees that electrotonic interaction between the two electrodes will be small or negligible, and therefore the unipolar and bipolar electrodes should yield identical results as observed in this study.

Pacing Lead Embodiments

The present invention can be embodied in epicardial and endocardial pacing leads of the types known in the prior art. A first embodiment of a pacing lead that both forms a discontinuity and provides pacing stimulation is depicted in FIGS. 15–19. The endocardial pacing lead 10 comprising a lead body 26 extending between a proximal connector assembly 20 and a distal electrode head 50. A stylet 30 is also depicted in FIG. 15 having an elongated stylet wire 32 extending from a stylet knob 34 and inserted down the lumen of the lead body 26.

Lead body 26 is formed of a length of outer insulating sheath 12 having proximal and distal ends and a sheath lumen, the sheath 12 operating as an electrical insulator formed of a biocompatible silicone rubber or polyurethane compound substantially inert to body fluids. A multi-filar, coiled wire conductor 18 having proximal and distal ends and a coil lumen formed therein is loosely received within the sheath lumen of sheath 12.

The proximal connector assembly 20 comprises a connector ring 22 and a connector pin 24 that are electrically connected to separately insulated anodic and cathodic wires of the multi-filar coiled wire conductor 18. Sealing ring sets 28 and 28' are compressed and serve to seal the lead body lumen and the gap between the connector pin 24 and connector ring 22 from ingress of body fluids upon insertion of connector assembly 20 into a mating bore of an implantable pulse generator connector block in a manner well known in the art.

Figure 18:
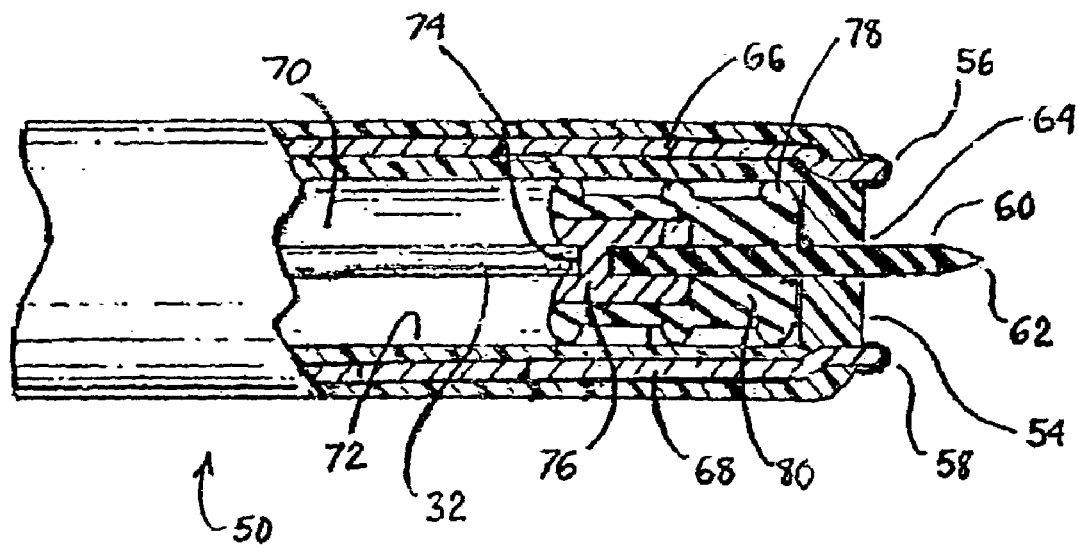
FIG. 18 is an expanded side view in partial cross-section of the electrode head of the lead of FIG. 15 depicting the cutting blade extended to form a discontinuity in cardiac tissue between the anodic and cathodic pacing electrodes.
Figure 19:
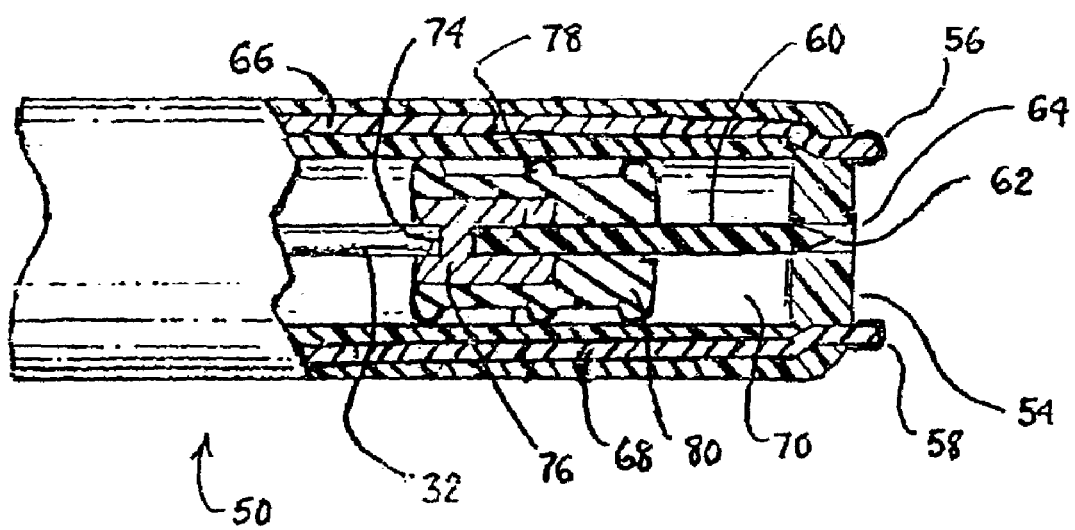
FIG. 19 is an expanded side view in partial cross-section of the electrode head of the lead of FIG. 15 depicting the cutting blade retracted into a chamber of the electrode head during transvenous advancement to an implantation site.

Sheath 12 and coiled wire conductor 18 extend between the connector assembly 20 and the electrode head 50 shown in cross-section in FIGS. 18 and 19. The electrode head 50 can include a plurality of soft, pliant tines 52 (shown in FIG. 15 but omitted from FIGS. 16–19 for convenience of illustration) that provide passive fixation of the electrode head 40 disposing the electrode head distal surface 54 against the endocardium in a manner well known in the art. Anodic and cathodic pacing electrodes 56 and 58 and a cutting element or blade 60 extend distally from the electrode head distal surface 54. The anodic and cathodic pacing electrodes 56 and 58 are electrically connected through the separately insulated anodic and cathodic wires of the multi-filar coiled wire conductor 18 to the connector ring 22 and connector pin 24, respectively.

The electrode head distal surface 54 is preferably non-conductive and supports the anodic and cathodic pacing electrodes 56 and 58 on either side of a centrally disposed cutting element or blade 60. The anodic and cathodic pacing electrodes 56 and 58 are spaced apart by an inter-electrode distance 2l; which may be on the order or 3.0 mm to 5.0 mm apart. The anodic and cathodic pacing electrodes 56 and 58 can be formed of any of the known pacing materials and have an electrode surface area of about 1–2 mm$^2$ or 1.2 mm$^2$ for example. The pacing electrodes 56 and 58 can be formed on the surface of the electrode head distal surface 54 or can project distally from the surface of the electrode head distal surface 54. The pacing electrodes 56 and 58 are coupled through conductors 66 and 68, respectively, to wires of the coiled wire conductor 18.

The cutting element or blade 60 is adapted to be retracted into the distal electrode head 50 during implantation as shown in FIG. 19 and ejected distally of the electrode head distal surface 54 at the implantation site to cut through the endocardium and form the discontinuity as shown in FIG. 18. The cutting element or blade 60 is preferably formed of a non-conductive ceramic or a similar material that can have a highly sharpened cutting edge 62. The cutting edge 62 preferably extends about 2 mm further distally when ejected as shown in FIG. 18 than the anodic and cathodic pacing electrodes 56 and 58.

The electrode head 50 of lead 10 is advanced via a percutaneous access into a vein with the cutting element or blade 60 retracted into a slit 64 and cylindrical chamber 70 of the electrode head 50 as shown in FIG. 19. A first stylet 30 having stylet wire 32 length that extends to the distal electrode head 40 can be used to stiffen and steer the lead body 26 during implantation.

A second stylet 30 having a stylet wire 32 length that extends through the length of the distal electrode head 40 can then be used to distally advance the cutting element or blade 60 from the distal electrode head 40 to form a lesion or cleft in endocardial tissue. The proximal end of the cutting blade 60 is mounted to a mounting block 76 embedded within a sealing block 80 having a plurality of sealing rings 78 bearing tightly against the surface of the cylindrical chamber 70. A proximal recess 74 of the movable mounting block 76 can be engaged by the distal surface of stylet wire 32. The stylet wire 32 is advanced distally within the lead body lumen to engage the recess 74 to move the assembly of the sealing block 80, the mounting block 76, and the cutting blade 60 distally from the retracted position of FIG. 19 to the extended position of FIG. 18.

The movement of the cutting blade 60 is done with sufficient force to penetrate through the cardiac tissue layers. The cutting edge 62 is shaped like the edge of a razor blade. The electrode head is firmly advanced against the cardiac tissue in initial implantation, and the tines hold the advanced position.

The present invention may also be employed in an epicardial pacing lead where it may not be necessarily necessary to move cutting element or blade. The electrode head 150 of an exemplary epicardial pacing lead 100 is depicted in part in FIGS. 20 and 21. The lead body 126, coiled wire conductor 118, and proximal connector assembly (not depicted) can take the forms employed in the endocardial lead 10, except that a stylet lumen and stylet are not necessary. The electrode head 150 is provided with a mesh 112 on the electrode head surface 154 adapted to encourage tissue ingrowth and that can be sutured through or adhered to the epicardium employing a medical adhesive following procedures known in the prior art.

Again, the anodic and cathodic pacing electrodes 156 and 158 are spaced apart by an inter-electrode distance 2l; which may be on the order or 3.0 mm to 5.0 mm apart. The anodic and cathodic pacing electrodes 156 and 158 can be formed of any of the known pacing materials and have an electrode surface area of about 1–2 mm$^2$ or 1.2 mm$^2$ for example. The pacing electrodes 156 and 158 can be formed on the surface of the electrode head distal surface 154 or can project distally from the surface of the electrode head distal surface 154. The pacing electrodes 156 and 158 are coupled through wires of the coiled wire conductor 118 to the connector pin and ring of the proximal connector assembly.

The movement of the cutting blade 160 is done with sufficient force to penetrate through the cardiac tissue layers. In this embodiment, the cutting blade 160 is shaped like an arrow that has a point 164 that first penetrates the tissue layer before the arrow edge 162 extending away from the point 164 cuts through the cardiac tissue.

Figure 22:
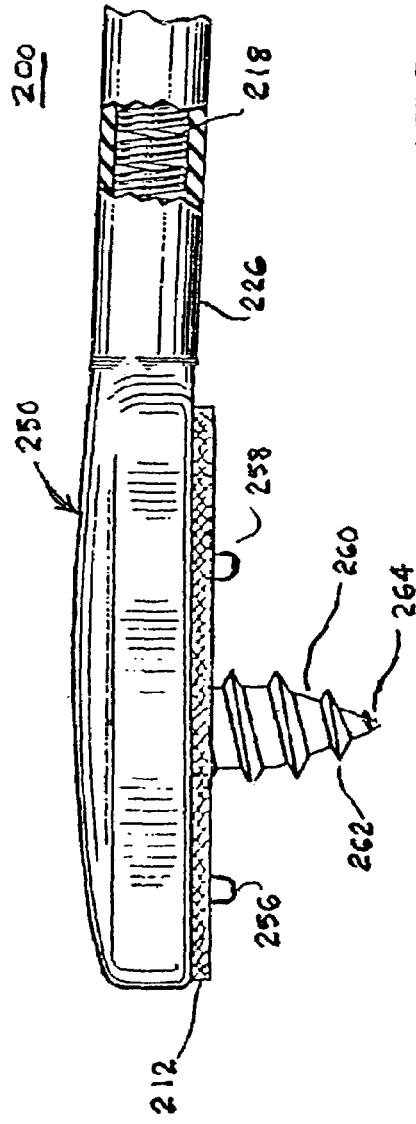
FIG. 22 is a side view of an electrode head of an epicardial pacing lead that supports a solid screw to form a discontinuity in cardiac tissue between the anodic and cathodic pacing electrodes.
Figure 23:
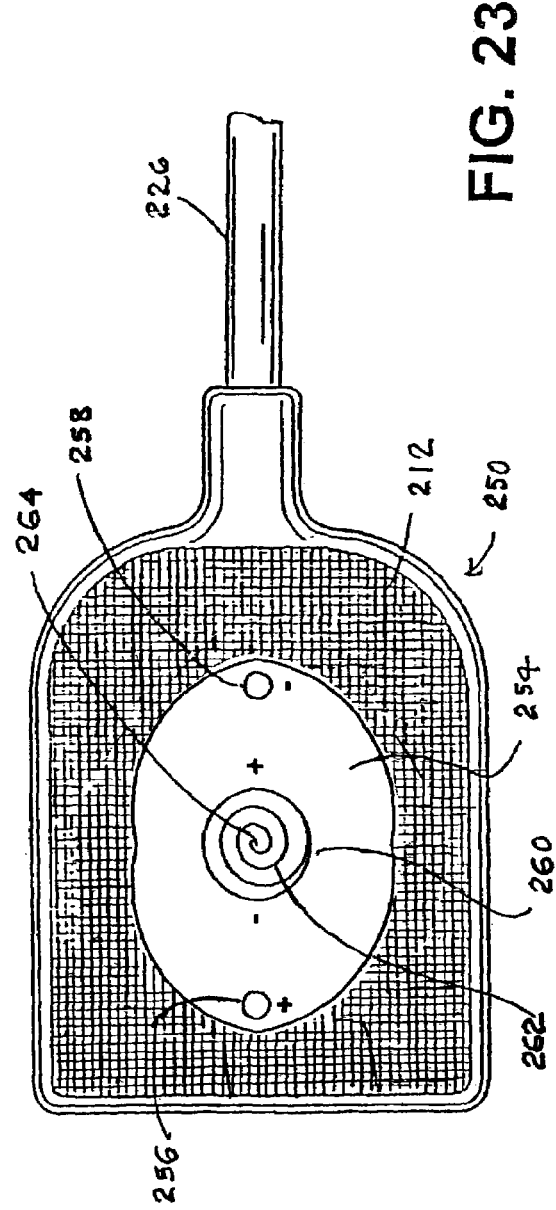
FIG. 23 is a bottom view of the electrode head of FIG. 21.

An electrode head 250 of a further exemplary epicardial pacing lead 200 that supports a solid, non-conductive, screw 260 to form a discontinuity in cardiac tissue between the anodic and cathodic pacing electrodes 256 and 258 is depicted in FIGS. 22 and 23. The lead body 226, coiled wire conductor 218, and proximal connector assembly (not depicted) can take the forms employed in the endocardial lead 10, except that a stylet lumen and stylet are not necessary.

Again, the anodic and cathodic pacing electrodes 256 and 258 are spaced apart by an inter-electrode distance 2l, which may be on the order or 3.0 mm to 5.0 mm apart. The anodic and cathodic pacing electrodes 256 and 258 can be formed of any of the known pacing materials and have an electrode surface area of about 1–2 mm$^2$ or 1.2 mm$^2$ for example. The pacing electrodes 256 and 258 can be formed on the surface of the electrode head distal surface 254 or can project distally from the surface of the electrode head distal surface 254. The pacing electrodes 256 and 258 are coupled through wires of the coiled wire conductor 218 to the connector pin and ring of the proximal connector assembly.

The electrode head 250 is provided with a mesh 212 adapted to encourage tissue ingrowth and that can be sutured through or adhered to the epicardium employing a medical adhesive following procedures known in the prior art. Or, fixation may be possible by the threads 262 of solid helix or screw 260 that are intended to be screwed into the myocardium employing a fixation tool, e.g., the tool disclosed in commonly assigned U.S. Pat. No. 6,010,526. The electrode head 250 is grasped by the tool and pressed against the epicardium as the tool and electrode head 250 are rotated so that sharpened tip 264 penetrates the epicardium, and the threads 262 screw into the myocardium and draw the epicardium against the pacing electrodes 256 and 258.

Although an epicardial lead is depicted in FIGS. 22 and 23, it will be understood that the solid helix or screw 260 can be substituted for the cutting blade 60 of the endocardial lead of FIGS. 15–19.

In each such embodiment, the virtual anode and virtual cathode are created in the cardiac tissue on the sides of the blade 60 or 160 or the screw 260 that are closest to the cathodic and anodic pacing electrodes as depicted in the figures.

It will be understood that the above-described embodiments are particularly useful for bipolar pacing as shown or for unipolar pacing, wherein the indifferent anodal pacing electrode 56, 156, 256 is not present or is not employed by the IPG.

CONCLUSION

All patents and publications identified herein are incorporated herein by reference in their entireties.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

We claim:

1. A method of applying pacing pulses to cardiac tissue having a myocardial space constant to effect depolarization of a cardiac tissue mass of a heart chamber comprising:

forming a discontinuity in the cardiac tissue of the heart chamber;

disposing a first pacing electrode at a distance approximately less than the space constant of the cardiac tissue from the discontinuity in the cardiac tissue;

disposing a second pacing electrode on a side of the discontinuity opposite the first pacing electrode and at a distance approximately less than the space constant of the cardiac tissue from the discontinuity in the cardiac tissue; and applying a stimulus to the cardiac tissue through the pacing electrodes to form a depolarization region at the pacing electrodes insufficient to propagate a depolarization wave front through the cardiac tissue mass of the heart chamber but sufficient to induce a transmembrane potential change at the tissue adjacent to the discontinuity that results in a propagated depolarization wave front to effect a contraction of the heart chamber.

2. The method of claim 1, wherein the step of forming a discontinuity comprises forming a lesion in the cardiac tissue.

3. The method of claim 1, wherein the step of forming a discontinuity comprises forming an intracellular cleft in the cardiac tissue.

4. The method of claim 1, wherein the step of forming a discontinuity comprises forming an intracellular cleft by applying a cutting blade to the cardiac tissue to cut the cardiac tissue.

5. The method of claim 1, wherein the step of forming a discontinuity comprises forming an intracellular cleft in the cardiac tissue by screwing a non-conductive, solid screw into the cardiac tissue.

6. The method of claim 1, wherein the step of forming a discontinuity comprises forming an intracellular cleft in the cardiac tissue by insertion of an electrically insulated member into the cardiac tissue.

7. The method of claim 1, wherein the step of forming a discontinuity comprises forming an intracellular cleft by applying an electrically insulated cutting blade to the cardiac tissue to cut the cardiac tissue and retaining the electrically insulated cutting blade in the intracellular cleft.

8. The method of claim 1, wherein the cardiac tissue comprises cardiac cells that are elongated in length and arranged in anisotropic cardiac fibers and the step of forming a discontinuity comprises forming an elongated discontinuity in the cardiac tissue extending in alignment with or transverse to the lengths of the elongated cardiac cells.

9. The method of claim 8, wherein the step of forming a discontinuity comprises applying a cutting blade to the cardiac tissue to cut the cardiac tissue.

10. The method of claim 8, wherein the step of forming a discontinuity comprises forming an intracellular cleft by applying an electrically insulated cutting blade to the cardiac tissue to cut the cardiac tissue and retaining the electrically insulated cutting blade in the intracellular cleft.

11. The method of claim 8, wherein the step of forming a discontinuity comprises forming an elongated intracellular cleft in the cardiac tissue by insertion of an electrically insulated member into the cardiac tissue.

12. A cardiac pacing lead of the type comprising an elongated cardiac lead body extending between a proximal electrode connector and a distal electrode head for applying pacing pulses to cardiac tissue having a myocardial space constant to effect depolarization of a cardiac tissue mass of a heart chamber comprising:

discontinuity forming means supported on the electrode head for forming a discontinuity in the cardiac tissue of the heart chamber;

a first pacing electrode supported by the electrode head and disposed on one side of the discontinuity forming means at a distance less than the space constant of the cardiac tissue from the discontinuity forming means; and a second pacing electrode supported by the electrode head and disposed on an opposite side of the discontinuity forming means at a distance less than the space constant of the cardiac tissue from the discontinuity forming means, wherein the discontinuity forming means comprises a non-conductive cutting blade supported to extend from the electrode head to be inserted into the cardiac tissue to cut the cardiac tissue.

13. The cardiac pacing lead of claim 12, wherein the discontinuity forming means comprises means for forming a lesion in the cardiac tissue.

14. The cardiac pacing lead of claim 12, wherein the non-conductive cutting blade includes a point supported to extend from the electrode head to be inserted into the cardiac tissue to cut the cardiac tissue.

15. The cardiac pacing lead of claim 12, wherein the discontinuity forming means comprises means for forming an intracellular cleft in the cardiac tissue.

16. The cardiac pacing lead of claim 12, wherein the discontinuity forming means comprises a solid, non-conductive, fixation screw supported to extend from the electrode head to be screwed into the cardiac tissue.

17. The cardiac pacing lead of claim 12, wherein the cardiac tissue comprises cardiac cells that are elongated in length and arranged in anisotropic cardiac fibers and the discontinuity forming means comprises means for forming an elongated discontinuity extending in alignment with or transverse to the lengths of the elongated cardiac cells.

18. The cardiac pacing lead of claim 17, wherein the discontinuity forming means comprises means for forming an elongated intracellular cleft in the cardiac tissue.

19. The cardiac pacing lead of claim 17, wherein the non-conductive cutting blade includes a point supported to extend from the electrode head to be inserted into the cardiac tissue to cut the cardiac tissue.

20. A method of applying pacing pulses to cardiac tissue having a myocardial space constant to effect depolarization of a cardiac tissue mass of a heart chamber comprising:

forming an elongated discontinuity in the cardiac tissue of the heart chamber having first and second discontinuity sides;

disposing an anodic pacing electrode at a distance less than the space constant of the cardiac tissue from the first side of the discontinuity in the cardiac tissue;

disposing a cathodic pacing electrode at a distance less than the space constant from the second side of the discontinuity in the cardiac tissue; and applying a stimulus of a first polarity to the cardiac tissue through the anodic and cathodic pacing electrodes to form a cathodic depolarization region at the cathodic pacing electrode insufficient in volume to propagate a depolarization wave front through the cardiac tissue mass of the heart chamber but sufficient to induce a transmembrane potential change at the tissue adjacent to the discontinuity that results in a propagated depolarization wave front to effect a contraction of the heart chamber.

21. The method of claim 20, wherein the step of forming a discontinuity comprises forming a lesion in the cardiac tissue between the anodic and cathodic pacing electrodes.

22. The method of claim 20, wherein the step of forming a discontinuity comprises forming an intracellular cleft in the cardiac tissue between the anodic and cathodic pacing electrodes.

23. The method of claim 20, wherein the step of forming a discontinuity comprises applying a cutting blade to the cardiac tissue to cut the cardiac tissue between the anodic and cathodic pacing electrodes.

24. The method of claim 20, wherein the step of forming a discontinuity comprises screwing a non-conductive solid screw into the cardiac tissue between the anodic and cathodic pacing electrodes.

25. The method of claim 20, wherein the cardiac tissue comprises cardiac cells that are elongated in length and arranged in anisotropic cardiac fibers and the step of forming a discontinuity comprises forming an elongated discontinuity in the cardiac tissue between the anodic and cathodic pacing electrodes in alignment with or transverse to the lengths of the elongated cardiac cells.

26. The method of claim 25, wherein the step of forming a discontinuity comprises forming an intracellular cleft by applying an electrically insulated cutting blade to the cardiac tissue to cut the cardiac tissue and retaining the electrically insulated cutting blade in the intracellular cleft between the anodic and cathodic pacing electrodes.

27. The method of claim 25, wherein the step of forming a discontinuity comprises forming an elongated intracellular cleft in the cardiac tissue by insertion of an electrically insulated member into the cardiac tissue between the anodic and cathodic pacing electrodes.

28. The method of claim 25, wherein the step of forming a discontinuity comprises applying a cutting blade to the cardiac tissue to cut the cardiac tissue between the anodic and cathodic pacing electrodes.

29. The method of claim 25, wherein the step of forming a discontinuity comprises forming a lesion in the cardiac tissue between the anodic and cathodic pacing electrodes.

30. A cardiac pacing lead of the type comprising an elongated cardiac lead body extending between a proximal electrode connector and a distal electrode head for applying pacing pulses to cardiac tissue having a myocardial space constant to effect depolarization of a cardiac tissue mass of a heart chamber comprising:

discontinuity forming means supported on the electrode head for forming an elongated discontinuity having first and second sides in the cardiac tissue of the heart chamber;

an anodic pacing electrode supported by the electrode head and disposed at a distance less than the space constant of the cardiac tissue from the first side of the discontinuity forming means; and a cathodic pacing electrode supported by the electrode head and disposed at a distance less than the space constant of the cardiac tissue from the second side of the discontinuity forming means, the discontinuity forming means comprises a non-conductive cutting blade supported to extend from the electrode head to be inserted into the cardiac tissue between the anodic and cathodic pacing electrodes to cut the cardiac tissue.

31. The cardiac pacing lead of claim 30, wherein the discontinuity forming means comprises means for forming a lesion in the cardiac tissue between the anodic and cathodic pacing electrodes.

32. The cardiac pacing lead of claim 30, wherein the non-conductive cutting blade includes a point supported to extend from the electrode head to be inserted into the cardiac tissue between the anodic and cathodic pacing electrodes to cut the cardiac tissue.

33. The cardiac pacing lead of claim 30, wherein the discontinuity forming means comprises means for forming an intracellular cleft in the cardiac tissue between the anodic and cathodic pacing electrodes.

34. The cardiac pacing lead of claim 30, wherein the discontinuity forming means comprises a solid, non-conductive, fixation screw supported to extend from the electrode head between the anodic and cathodic pacing electrodes to be screwed into the cardiac tissue.

35. The cardiac pacing lead of claim 30, wherein the cardiac tissue comprises cardiac cells that are elongated in length and arranged in anisotropic cardiac fibers and the discontinuity forming means comprises means for forming an elongated discontinuity between the anodic and cathodic pacing electrodes extending in alignment with or transverse to the lengths of the elongated cardiac cells.

36. The cardiac pacing lead of claim 35, wherein the discontinuity forming means comprises means for forming an elongated intracellular cleft in the cardiac tissue between the anodic and cathodic pacing electrodes.

37. The cardiac pacing lead of claim 35, wherein the non-conductive cutting blade includes a point supported to extend from the electrode head between the anodic and cathodic pacing electrodes to be inserted into the cardiac tissue to cut the cardiac tissue.

38. The cardiac pacing lead of claim 35, wherein the discontinuity forming means comprises means for forming a lesion in the cardiac tissue between the anodic and cathodic pacing electrodes.

\* \* \* \* \*